US006296785B1

(12) United States Patent
Nelson et al.

(10) Patent No.: US 6,296,785 B1
(45) Date of Patent: Oct. 2, 2001

(54) INDENO-FUSED PHOTOCHROMIC NAPHTHOPYRANS

(75) Inventors: Clara M. Nelson; Anu Chopra, both of Pittsburgh; Olga G. Petrovskaia, Monroeville; David B. Knowles, Apollo; Barry Van Gemert, Murrysville; Anil Kumar, Pittsburgh, all of PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/656,510

(22) Filed: Sep. 6, 2000

Related U.S. Application Data
(60) Provisional application No. 60/154,428, filed on Sep. 17, 1999, and provisional application No. 60/164,653, filed on Nov. 10, 1999.

(51) Int. Cl.[7] ...................... C07D 311/78; C07D 405/04; G02B 5/23

(52) U.S. Cl. ........................... 252/586; 549/382; 544/150

(58) Field of Search ........................... 549/382; 544/150; 252/586

(56) References Cited

U.S. PATENT DOCUMENTS

| | | | |
|---|---|---|---|
| 3,361,706 | 1/1968 | Meriwether et al. | 260/39 |
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,971,872 | 7/1976 | LeBeouf | 428/412 |
| 4,215,010 | 7/1980 | Hovey et al. | 252/300 |
| 4,342,668 | 8/1982 | Hovey | 252/586 |
| 4,719,296 | 1/1988 | Irie et al. | 544/71 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,873,029 | 10/1989 | Blum | 264/1.3 |
| 4,880,667 | 11/1989 | Welch | 427/160 |

(List continued on next page.)

FOREIGN PATENT DOCUMENTS

| | | |
|---|---|---|
| WO 97/48762 | 12/1997 | (WO) . |
| WO 99/15518 | 4/1999 | (WO) . |
| 19902771 | 6/1999 | (WO) . |

OTHER PUBLICATIONS

Van Gemert and Kish, PPG Technology Journal, vol. 5, "The Intricacies of Color Matching Organic Photochromic Dyes",p 53–61, 1999.
Friedel–Crafts and Related Reactions, George Olah, Interscience Publishers, 1964, vol. 3, Chapter XXXI (Aromatic Ketone Synthesis).
"Regioselective Friedel–Crafts Acylation of 1,2,3,4–Tetrahydroquinoline and Related Nitrogen Heterocycles: Effects of NH Protective Groups and Ring Size" by Ishihara, Yugi et al., J. Chem. Soc., Perkin Trans. 1, p 3401–3406, 1992.
S. Patai and S. Dayagi, J. Chem. Soc. 1962, "Tritylation and Detritylation of Active Methylene Compounds", p 716–723.
G. Chuchani, J. Chem. Soc. 1959, "Titylation of ortho–D-isubstituted Benzenes. Systematic Differences of Activation of ortho– and para Directing Groups", p 1753–1756.
F. G. Baddar et al., J. Chem. Soc., 1958, "1–Phenylnaphthalenes. Part IV.* The Cylcisation of Methyl Hydrogen cis and trans–λ–o–Methoxyphenyl– and Ethyl Hydrogen cis– and trans–λ–o–p–Methoxyphenyl–λ–phenylitaconate to the Corresponding 1–Phenylnaphthalenes", p 986.
C. F. Koesch, Journal of Organic Chemistry, vol. 26, "Behavior of x–Substituted Chalcones on Attempted Friedel–Crafts Arylation", p 2590–2592, 1961.

Primary Examiner—Deborah C. Lambkin
Assistant Examiner—Andrea M. D'Souza
(74) Attorney, Agent, or Firm—Frank P. Mallak

(57) ABSTRACT

Described are novel photochromic indeno-fused naphthopyran compounds, examples of which include naphthopyran compounds having a substituted or unsubstituted indeno group, the 2,1 positions of which are fused to the naphtho portion of the naphthopyran as shown below. Also present on the naphthopyran are moderate to strong electron donor substituents at the number 6- and 7-positions and optionally at the 8-position of the pyran ring or a cyclic group fused to the h side of the naphtho portion and weak to moderate electron donor substiuents at the 3-position of the pyran ring. Certain substituents may also be present at the number 5, 8, 9, 10, 11, 12, or 13 carbon atoms of the compounds. These compounds have a rating of at least 80 in the Relative ΔOD at Saturation Test and may be represented by the following graphic formula:

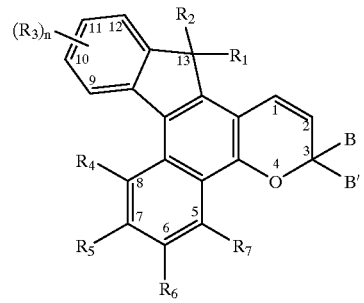

Also described are polymeric organic host materials that contain or that are coated with such compounds. Optically clear articles such as ophthalmic lenses or other plastic transparencies that incorporate the novel naphthopyran compounds or combinations thereof with complementary photochromic compounds, e.g., certain other naphthopyrans, benzopyrans, and spiro(indoline)type compounds, are also described.

23 Claims, No Drawings

U.S. PATENT DOCUMENTS

| | | | |
|---|---|---|---|
| 4,931,219 | 6/1990 | Kwiatkowski et al. | 252/586 |
| 4,931,220 | 6/1990 | Haynes et al. | 252/586 |
| 5,066,818 | 11/1991 | Van Gemert et al. | 549/389 |
| 5,166,345 | 11/1992 | Akashi et al. | 544/71 |
| 5,236,958 | 8/1993 | Miyashita | 518/121 |
| 5,238,981 | 8/1993 | Knowles | 524/110 |
| 5,252,742 | 10/1993 | Miyashita | 548/121 |
| 5,274,132 | 12/1993 | Van Gemert | 549/389 |
| 5,359,085 | 10/1994 | Iwamoto et al. | 548/468 |
| 5,384,077 | 1/1995 | Knowles | 252/586 |
| 5,405,958 | 4/1995 | Van Gemert | 544/71 |
| 5,429,774 | 7/1995 | Kumar | 252/586 |
| 5,458,814 | 10/1995 | Kumar et al. | 252/586 |
| 5,466,398 | 11/1995 | Van Gemert et al. | 252/586 |
| 5,488,119 | 1/1996 | Fischer-Reimann et al. | 552/201 |
| 5,514,817 | 5/1996 | Knowles | 549/384 |
| 5,552,090 | 9/1996 | Van Gemert et al. | 252/586 |
| 5,552,091 | 9/1996 | Kumar | 252/586 |
| 5,565,147 | 10/1996 | Knowles et al. | 252/586 |
| 5,573,712 | 11/1996 | Kumar et al. | 252/586 |
| 5,578,252 | 11/1996 | Van Gemert et al. | 252/586 |
| 5,637,262 | 6/1997 | Van Gemert et al. | 252/586 |
| 5,645,767 | 7/1997 | Van Gemert | 252/586 |
| 5,656,206 | 8/1997 | Knowles et al. | 252/586 |
| 5,658,500 | 8/1997 | Kumar et al. | 252/586 |
| 5,658,501 | 8/1997 | Kumar et al. | 252/586 |
| 5,674,432 | 10/1997 | Knowles et al. | 252/586 |
| 5,698,141 | 12/1997 | Kumar | 252/586 |
| 5,753,146 | 5/1998 | Van Gemert et al. | 252/586 |
| 5,936,016 | 8/1999 | Lareginie et al. | 524/94 |
| 5,961,892 | 10/1999 | Van Gemert et al. | 252/586 |
| 5,965,630 | 10/1999 | Imafuku et al. | 523/106 |
| 5,965,631 | 10/1999 | Nicholson et al. | 523/106 |
| 6,113,814 | 9/2000 | Van Gemert et al. | 252/586 |

INDENO-FUSED PHOTOCHROMIC NAPHTHOPYRANS

CROSS REFERENCE TO RELATED APPLICATIONS

This application claims the benefit of U.S. provisional application Serial No. 60/154,428, filed Sep. 17, 1999 and U.S. provisional application Serial No. 60/164,653, filed Nov. 10, 1999.

DESCRIPTION OF THE INVENTION

The present invention relates to certain novel naphthopyran compounds. More particularly, this invention relates to novel indeno-fused photochromic naphthopyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion.

While the activated form of a typical organic photochromic molecule absorbs in the visible region over a relatively narrow range (Van Gemert and Kish, PPG Technology Journal, Vol. 5, pg. 53–61, 1999), broader absorbing naphthopyrans (i.e. those having two absorption bands), are not unknown. U.S. Pat. No. 5,645,767 discloses photochromic indeno[2,1-f]naphtho[1,2-b]pyrans having a blue/gray activated color. A blue/gray color will be perceived when there is a major absorption of visible light in the 580–620 nm range coupled with a minor absorption in the 420–500 nm range.

International Patent Application Publication No. WO 99/15518 discloses photochromic indeno[2,1-f]naphtho[1,2-b]pyrans having a green activated color. A green color will be perceived when there is a major absorption of visible light in the 580–620 nm range coupled with a major absorption of roughly equal intensity in the 400–480 nm range.

While it is obvious from the previous description that it is possible to obtain many complex activated colors, it is not disclosed in the aforementioned patent or application how to select substituents for both the pyrano and the indeno-fused naphtho portions of the indeno[2,1-f]naphtho[1,2-b]pyran in order to control the wavelength and/or intensity of the absorbance bands within the activated visible spectra.

The present invention discloses what types of substituents and where they may be placed in order to control the wavelength and/or intensity of the visible absorbance bands of indeno[2,1-f]naphtho[1,2-b]pyrans having 2 intense spectral bands in the visible spectrum.

These novel naphthopyrans are substituted with weak to moderate electron donor groups at the 3-position of the pyran ring and have either moderate to strong electron donor groups at the 6- and 7-position or a cyclic group fused to the h face. The compounds may optionally have at the 8-position moderate to strong electron donor groups and may have other substituents at the 5-, 8-, 9-, 10-, 11-, 12- or 13-positions of the compound. The selection and placement of these substituents being so that that the photochromic compounds of the present invention have a rating of at least 80 in the Relative $\Delta$OD at Saturation Test, described hereinafter.

Generally, the activated (colored) form of these photochromic compounds have an optical density of band "A" which is of greater intensity than the optical density of band "B". The absorption of band "A" occurs in the 420–500 nm region while the absorption of band "B" occurs in the 500–650 nm region of the activated visible spectrum. These compounds exhibit an apparent blended gray, brown or green activated color. The use of certain individual compounds of the present invention substantially eliminates the need for combining two or more compounds to obtain neutral colors such as gray or brown. In addition, these compounds have demonstrated a high molar absorptivity (or molar extinction coefficient) in the ultraviolet (UV) light range, an acceptable fade rate without the addition of acids or bases, a high activated intensity and a high coloration rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel indeno[2,1-f]naphtho[1,2-b] pyrans having two absorption bands in the activated (colored) state, an acceptable fade rate, high activated intensity, a high coloration rate and a rating of 80 or higher in the Relative $\Delta$OD at Saturation Test may be prepared. The Relative $\Delta$OD at Saturation Test is described in Example 21. The ratings of the test are defined herein as the result obtained when the optical density of band "A" is divided by the optical density of band "B" and multiplied by 100. It is believed that compounds having a rating of 80 or higher are most valuable for formulating neutral grays, greens and browns for commercial photochromic ophthalmic eyeware.

The naphthopyrans of the present invention may have a rating in the Relative ΔOD at Saturation Test of at least 80, preferably at least 90, more preferably from 90 to 150 and most preferably, from 100 to 130. The rating is expected to be less than 500, preferably less than 400, more preferably less than 300 and most preferably less than 200. The rating for the naphthopyrans may range between any combination of these values, inclusive of the recited values, e.g., from at least 80 to less than 500. The naphthopyrans of the present invention may have a rating greater than 500 if the two absorption bands are distinguishable and an optical density is obtainable for the calculation.

Preparation of such compounds is achieved by balancing the effects of the potential substituents as described hereinafter. For example, the "A" band of these compounds can be enhanced relative to the "B" band by employing strong electron donor substituents in the 7-position, moderate electron donors in the 6-position, and weak to moderate electron donors in the 3-position of the pyran ring. Compounds having relatively equivalent intensity for the "A" and "B" bands can be obtained by having electron donors of relatively equal intensity at the 6- and 7-positions and weak to moderate electron donors at the 3-position of the pyran ring. Strong electron donors on an aryl grouping at the 3-position of the pyran will enhance the "B" band relative to the "A" band. The intensity or strength of the electron donors at the 3-position of the pyran ring will not only effect the relative intensity of the two spectral bands, but also their position. For example, strong electron donors on an aryl grouping at the 3-position will shift both bands bathochromically (the "B" band more than the "A" band).

The relative strength of electron donor groups is frequently described by Hammett Sigma values (specifically $\sigma_p$ values). A tabular listing of $\sigma_p$ constants for a variety of substituents can be found in "Exploring QSAR, Hydrophobic, Electronic, and Steric Constants, C. Hansch, A. Leo, and D. Hoekman, Eds., Published by The American Chemical Society, Washington, D.C., 1995, which disclosure is incorporated herein by reference. Examples of strong electron donors, defined herein as having a Hammett $\sigma_p$ value of between −1.0 and −0.5, that may be used at the 6- and 7-positions or at the para position of an aryl grouping present at the 3-position of the pyrano portion of the naphthopyran include amino, monoalkylamino, dialkylamino, morpholino, and piperidino. Examples of moderate electron donors, defined herein as having a $\sigma_p$ value of between −0.49 and −0.20 that may be used at the 6- and 7-positions or at the para position of an aryl grouping present at the 3-position of the pyrano portion of the naphthopyran include ethoxy, methoxy, and p-aminophenyl. Examples of weak electron donors, defined herein as having a Hammett $\sigma_p$ value of between −0.01 and −0.19 that may be used at the 3-position of the pyrano portion of the naphthopyran include methyl, ethyl, phenyl, naphthyl, and tolyl.

The compounds may be described as naphthopyrans of indeno[2,1-f]naphtho[1,2-b]pyran structure which are characterized by having moderate to strong electron donor groups $R_5$, and $R_6$, at the 7 and 6 positions, respectively, or a cyclic group fused to the h face, moderate to strong electron donors optionally, at the 8 position, weak to moderate electron donor substituents at the 3-position and a rating of at least 80 in the Relative ΔOD at Saturation Test. These compounds may have certain other substituents at the number 5, 8, 9, 10, 11, 12, or 13 carbon atoms of the indeno-fused portion of the compound.

The compounds of the present invention may be represented by the following graphic formula I in which the letters a through u on the outside of the ring structure represent the faces or sides of the indeno-fused naphthopyran ring, and the numbers on the inside of the ring structure represent the positions of the ring atoms of the naphthopyran:

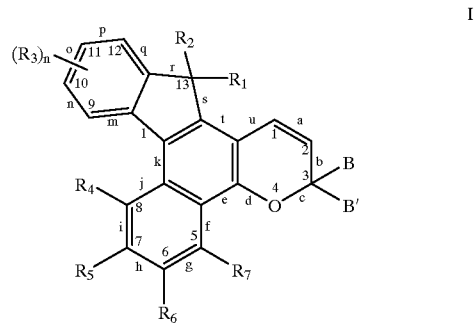

In graphic formula I, $R_1$ and $R_2$ may each be selected from the group consisting of:

(i) hydrogen, hydroxy, $C_1$–$C_6$ alkyl, amino, mono- or di-substituted amino, $C_3$–$C_7$ cycloalkyl, allyl, benzyl, mono-substituted benzyl, chloro, fluoro, the group —C(O)W, wherein W is hydroxy, $C_1$–$C_6$ alkyl, $C_1$–$C_6$ alkoxy, phenyl, mono-substituted phenyl, amino, mono ($C_1$–$C_6$)alkylamino or di($C_1$–$C_6$)alkylamino, e.g. N,N-dimethyl amino, N-methyl-N-propyl amino, etc., morpholino, piperidino or pyrrolidyl, said amino substituents being selected from the group consisting of $C_1$–$C_6$ alkyl, phenyl, benzyl and naphthyl, and said benzyl and phenyl substituents being $C_1$–$C_6$ alkyl or $C_1$–$C_6$ alkoxy;

(ii) the unsubstituted, mono- di-or trisubstituted groups phenyl, naphthyl, phenanthryl, pyrenyl, quinolyl, isoquinolyl, benzofuranyl, thienyl, benzothienyl, dibenzofuranyl, dibenzothienyl, carbazolyl, indolyl, said group substituents in this section (ii) being selected from the group consisting of chloro, fluoro, $C_1$–$C_6$ alkyl and $C_1$–$C_6$ alkoxy;

(iii) monosubstituted phenyl having a substituent at the para position that is a linking group, —(CH$_2$)$_t$— or —O—(CH$_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho [1,2-b]pyran;

(iv) the group, —OR$_8$, wherein R$_8$ is $C_1$–$C_6$ alkyl, $C_1$–$C_6$ acyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, benzoyl, monosubstituted benzoyl, naphthoyl or monosubstituted naphthoyl, said benzoyl and naphthoyl group substituents being $C_1$–$C_6$ alkyl or $C_1$–$C_6$ alkoxy, or R$_8$ is the group, —CH(R$_9$)Q, wherein R$_9$ is hydrogen or $C_1$–$C_3$ alkyl and Q is —CN, —CF$_3$, or —COOR$_{10}$, wherein R$_{10}$ is hydrogen or $C_1$–$C_3$ alkyl, or R$_8$ is the group, —C(O)V, wherein V is hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, the unsubstituted, mono- or di-substituted aryl groups, phenyl and naphthyl, amino, mono($C_1$–$C_6$)alkylamino, di($C_1$–$C_6$) alkylamino, phenylamino, mono- or di-($C_1$–$C_6$)alkyl substituted phenylamino, or mono- or di-($C_1$–$C_6$) alkoxy substituted phenylamino, said aryl group substituents being $C_1$–$C_6$ alkyl or $C_1$–$C_6$ alkoxy;

(v) the group —CH(Q')2 wherein Q' is —CN or —COOR$_{11}$, wherein R$_{11}$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, or the unsubstituted, mono- or di-substituted aryl groups phenyl or naphthyl, said aryl group substituents being $C_1$–$C_6$ alkyl or $C_1$–$C_6$ alkoxy;

(vi) the group —CH(R$_{12}$)G, wherein R$_{12}$ is hydrogen, $C_1$–$C_6$ alkyl or the unsubstituted, mono- or di-substituted aryl groups phenyl and naphthyl, and G is —COOR$_{11}$, —C(O)R$_{13}$ or —CH$_2$OR$_{14}$, wherein R$_{13}$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$)alkylamino, e.g., dimethyl amino, methyl propyl amino, etc., phenylamino, mono- or di-($C_1$–$C_6$)alkyl substituted phenylamino, mono- or di($C_1$–$C_6$)alkoxy substituted phenylamino, diphenylamino, mono- or di($C_1$–$C_6$) alkyl substituted diphenylamino, i.e., each phenyl has one or two $C_1$–$C_6$ alkyl substituents, mono- or di($C_1$–$C_6$)alkoxy substituted diphenylamino, i.e., each phenyl has one or two $C_1$–$C_6$ alkoxy substituents, morpholino, or piperidino, wherein R$_{14}$ is hydrogen, —C(O)R$_{11}$, $C_1$–$C_6$ alkyl, $C_1$–$C_3$ alkoxy($C_1$–$C_6$)alkyl, phenyl($C_1$–$C_3$)alkyl, mono($C_1$–$C_6$)alkoxy substituted phenyl($C_1$–$C_3$)alkyl, or the unsubstituted, mono- or di-substituted aryl groups phenyl or naphthyl, each of said aryl group substituents being $C_1$–$C_6$ alkyl or $C_1$–$C_6$ alkoxy; and (vii) the polyalkoxylated group T represented by the formula:

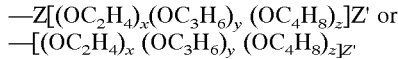

wherein —Z is —C(O)- or —CH2— and Z' is $C_1$–$C_3$ alkoxy or a polymerizable group i.e., any functional group capable of participating in a polymerization reaction. Polymer forming methods in which the polymerizable compounds of the present invention may participate include radical polymerization, and such other polymerization processes as are described in *Ullmann's Encyclopedia of Industrial Chemistry*, "Polymerization Processes", Vol. 21A, pp 305 to 428, which disclosure is incorporated herein by reference. The polymerizable groups may be selected from the group consisting of hydroxy, (meth)acryloxy, and epoxy, e.g., oxiranylmethyl. When there are 2 or more polymerizable groups on the naphthopyran, they may be the same or different.

The group, —(OC$_2$H$_4$)$_x$—, represents poly(ethylene oxide); —(OC$_3$H$_6$)$_y$—, represents poly(propylene oxide); and, —(OC$_4$H$_8$)$_z$—, represents poly(butylene oxide). When used in combination, the poly(ethylene oxide), poly (propylene oxide) and poly(butylene oxide) groups of T may be in a random or block order within the T moiety. The letters x, y and z are each a number between 0 and 50 and the sum of x, y and z is between 2 and 50. The sum of x, y and z may be any number that falls within the range of 2 to 50, e.g., 2, 3, 4 . . . 50. This sum may also range from any lower number to any higher number within the range of 2 to 50, e.g., 6 to 50, 31 to 50. The numbers for x, y, and z are average values and can be partial numbers, e.g., 9.5.

Alternatively, R$_1$ and R$_2$ may together form an oxo group, a spiro-carbocyclic ring containing 3 to 6 carbon atoms or a spiro-heterocyclic group containing 1 or 2 oxygen atoms and 3 to 6 carbon atoms including the spirocarbon atom and both rings may be benz-annelated with one or two benzene groups. The spiro-carbocyclic ring and spiro-heterocyclic group may also be substituted with one or two substituents selected from hydrogen or $C_1$–$C_6$ alkyl. Examples of the spiro-carbocyclic ring substituents include spirofluoreno, spirocyclopropyl, spirocyclobutyl, spirocyclopentyl, spirocyclohexyl, spiroindan-1-yl, spiroindan-2-yl, etc. Examples of the spiro-heterocyclic group include spiroxantheno and compounds which may be represented by the expression (-0-($C_2$–$C_5$ alkanediyl)-0-), e.g., spiro-1,3-dioxolane-2, spiro-1,3-dioxane-2, etc. or spirolactones such as butyrolactone, propiolactone etc. In the definitions of R$_1$ and R$_2$, like substituents have like meanings.

Preferably, R$_1$ and R$_2$ are each selected from the group consisting of hydrogen, hydroxy, $C_1$–$C_4$ alkyl, $C_3$–$C_6$ cycloalkyl, chloro, fluoro and the group, —OR$_8$, wherein R$_8$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$)alkyl, $C_1$–$C_3$ chloroalkyl, $C_1$–$C_3$ fluoroalkyl, the group, —CH(R$_9$) Q, wherein R$_9$ is hydrogen or $C_1$–$C_2$ alkyl and Q is —CN or —COOR$_{10}$, R$_{10}$ being hydrogen or $C_1$–$C_2$ alkyl, or R$_8$ is the group, —C(O)V, wherein V is hydrogen, $C_1$–$C_3$ alkoxy, phenyl, naphthyl, the mono-substituted aryl groups, phenyl or naphthyl, phenoxy, mono- or di-($C_1$–$C_3$)alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, each of said aryl group substituents being $C_1$–$C_3$ alkyl or $C_1$–$C_3$ alkoxy, or R$_1$ and R$_2$ are each the group T wherein x and y are each a number between 0 and 50, z is 0 and the sum of x and y is between 2 and 50, and more preferably, x is a number between 2 and 50, and y and z are each 0. More preferably, R$_1$ and R$_2$ are each hydrogen, hydroxy, $C_1$–$C_3$ alkyl or the group, —OR$_8$, wherein R$_8$ is $C_1$–$C_3$ alkyl.

Each R$_3$ in graphic formula I may be group T, $C_1$–$C_6$ alkyl, $C_1$–$C_6$ alkoxy, $C_3$–$C_7$ cycloalkyl, phenyl, benzyl, di($C_1$–$C_6$)alkylamino, dicyclohexylamino, diphenylamino, piperidyl, morpholinyl, pyridyl, bromo, chloro, fluoro, or the group —C(O)W, and n is the integer 0, 1, or 2, or when n is 2 and the R$_3$ groups are adjacent, the R$_3$ groups may together form a fused carbocyclic or a fused heterocyclic ring selected from the group consisting of benzo, pyridino, pyrazino, pyrimidino, furano, dihydrofurano and thiopheno, said ring being fused to the n, o or p sides of the indeno-fused naphthopyran. Preferably, R$_3$ is $C_1$–$C_6$ alkyl, $C_1$–$C_6$ alkoxy, chloro or fluoro, and n is the integer 0, 1, or 2. More preferably, R$_3$ is $C_1$–$C_3$ alkoxy and n is the integer 0, 1 or 2.

In graphic formula I, the substituents R$_5$, R$_6$ and optionally R$_4$ are moderate to strong electron donating groups defined herein. When R$_4$ is not a moderate to strong electron donating group, it may be selected from the same group of substituents as R$_7$, specifically hydrogen, $C_1$–$C_6$ alkyl, chloro, or fluoro. Preferably, R$_4$ and R$_7$ are each selected from hydrogen, $C_1$–$C_3$ alkyl, chloro or fluoro, and more preferably hydrogen. The moderate to strong electron donating groups of R$_5$ and R$_6$ and optionally R$_4$, may be selected from:

(i) the group, —OR$_8$', wherein R$_8{}^1$ is phenyl($C_1$–$C_3$)alkyl, $C_1$–$C_6$ alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, or R$_8$' is the group, —CH(R$_9$)Q, wherein R$_9$ is hydrogen or $C_1$–$C_3$ alkyl and Q is as defined before; and (ii) a group selected from:
  (1) —N($R_{15}$)$R_{16}$, wherein $R_{15}$ and $R_{16}$ are each selected from the group consisting of hydrogen, $C_1$–$C_8$ alkyl, phenyl, naphthyl, the heteroaromatic groups furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl and $C_1$–$C_{20}$ alkoxyalkyl, wherein said aryl group is phenyl or naphthyl;
  (2) a nitrogen containing ring represented by the following graphic formula:

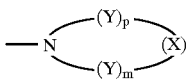

IIA wherein Y is selected from the group consisting of —$CH_2$—, —CH($R_{17}$)—, —C($R_{17}$)($R_{17}$)—, —CH(aryl)—, —C(aryl)$_2$—, and —C($R_{17}$)(aryl)—, and X is selected from the group consisting of —Y—, —O—, —S—, —S(O)—, —S($O_2$)—, —NH—, —$NR_{17}$— and —N-aryl, wherein $R_{17}$ is $C_1$–$C_6$ alkyl, said aryl substituent is phenyl or naphthyl, m is the integer 1, 2 or 3, and p is the integer 0, 1, 2, or 3, provided that when p is 0, X is Y; and
  (3) a group represented by the following graphic formulae:

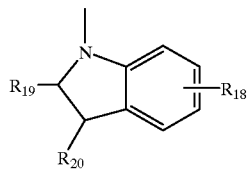

IIB

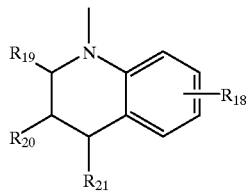

IIC wherein $R_{19}$, $R_{20}$ and $R_{21}$ are each hydrogen, $C_1$–$C_5$ alkyl, phenyl or naphthyl, or the groups $R_{19}$ and $R_{20}$ may come together to form a ring of 5 to 8 carbon atoms (including the ring carbon atoms). For example, when $R_{19}$ and $R_{20}$ come together to form a ring of 6 carbon atoms on the group represented by graphic formula IIB, the resulting unsaturated group is carbazol-9-yl and the saturated group is tetrahydrocarbazol-9-yl. $R_{18}$ is $C_1$–$C_6$ alkyl, $C_1$–$C_6$ alkoxy, fluoro or chloro; or (iii) $R_5$ and $R_6$ together form the following graphic formula;

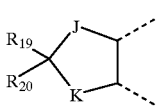

IID

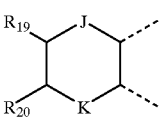

IIE wherein J and K are each oxygen or the group —$NR_{15}$—, $R_{15}$, $R_{19}$ and $R_{20}$ being as defined before. Preferably, $R_5$ and $R_6$ and optionally $R_4$, are each selected from the group consisting of:
  (i) the group, —$OR_8'$, wherein $R_8'$ is —CH($R_9$)Q and Q is —CN; and
  (ii) a group selected from:
    (1) —N($R_{15}$)$R_{16}$, wherein $R_{15}$ and $R_{16}$ are $C_1$–$C_4$ alkyl;
    (2) a nitrogen containing ring represented by graphic formula IIA wherein Y is —$CH_2$— or —CH($R_{17}$)—, X is —O—, —NH— or —$NR_{17}$— and $R_{17}$ is $C_1$–$C_3$ alkyl; or
    (3) a group represented by graphic formulae IIB or IIC wherein $R_{19}$, $R_{20}$ and $R_{21}$ are each hydrogen or $C_1$–$C_3$ alkyl and $R_{18}$ is $C_1$–$C_3$ alkyl; or
  (iii) $R_5$ and $R_6$ together form the group represented by graphic formulae IID and IIE wherein J and K are oxygen. More preferably, $R_4$, $R_5$ and $R_6$ are each $C_1$–$C_3$ alkoxy.

B and B' in graphic formula I may each be selected from the group consisting of:
  (i) mono-T-substituted phenyl;
  (ii) the unsubstituted, mono-, di-, and tri-substituted aryl groups, phenyl and naphthyl;
  (iii) 9-julolidinyl and the unsubstituted, mono- and di-substituted aromatic heterocyclic groups pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of said aryl and aromatic heterocyclic substituents in these parts (ii) and (iii) being selected from the group consisting of hydroxy, aryl, i.e., phenyl and naphthyl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, each aryl group described for said aryl or heteroaromatic substituent being phenyl or naphthyl;
  (iv) the unsubstituted or mono-substituted groups pyrazolyl, imidazolyl, pyridyl, pyrazolinyl, imidazolinyl, pyrrolinyl, phenothiazinyl, phenoxazinyl, phenazinyl or acridinyl, each of said substituents in this part (iv) being selected from the group consisting of $C_1$–$C_6$ alkyl, $C_1$–$C_6$ alkoxy, phenyl, fluoro, chloro and bromo;

(v) monosubstituted phenyl, having a substituent at the para position that is a linking group, —$(CH_2)_t$— or —O—$(CH_2)_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;

(vi) the groups represented by the following graphic formulae:

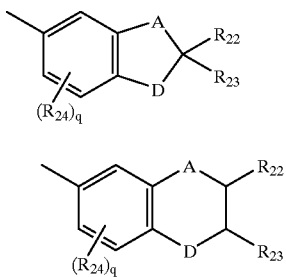

IIF

IIG wherein A may be methylene or oxygen and D may be oxygen or substituted nitrogen, provided that when D is substituted nitrogen, A is methylene, said nitrogen substituents being selected from the group consisting of hydrogen, $C_1$–$C_6$ alkyl, and $C_2$–$C_6$ acyl; each $R_{24}$ is $C_1$–$C_6$ alkyl, $C_1$–$C_6$ alkoxy, hydroxy, chloro or fluoro; $R_{22}$ and $R_{23}$ are each hydrogen or $C_1$–$C_6$ alkyl; and q is the integer 0, 1, or 2;

(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)cycloalkyl, chloro($C_3$–$C_6$)cycloalkyl, fluoro($C_3$–$C_6$)cycloalkyl and $C_4$–$C_{12}$ bicycloalkyl; and (viii) the group represented by the following graphic formula:

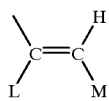

IIH wherein L in graphic formula IIH may be hydrogen or $C_1$–$C_4$ alkyl and M in graphic formula IIH may be selected from the unsubstituted, mono-, and di-substituted members of the group consisting of naphthyl, phenyl, furanyl, and thienyl, each of said group substituents in this part (viii) being $C_1$–$C_4$ alkyl, $C_1$–$C_4$ alkoxy, fluoro, or chloro.

Alternatively, B and B' may together form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane, and saturated $C_7$–$C_{12}$ spiro-tricyclic hydrocarbon rings, e.g., tricyclo[2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

More preferably, B and B' are each selected from the group consisting of: (i) phenyl, mono-substituted phenyl, and di-substituted phenyl, preferably substituted in the meta and/or para positions; (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, amino, mono($C_1$–$C_3$)alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIF and IIG, wherein A is methylene and D is oxygen, $R_{24}$ is $C_1$–$C_3$ alkyl or $C_1$–$C_3$ alkoxy, $R_{22}$ and $R_{23}$ are each hydrogen or $C_1$–$C_4$ alkyl; and q is the integer 0 or 1; (iv) $C_1$–$C_4$ alkyl; and (v) the group represented by the graphic formula IIH wherein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, $C_1$–$C_3$ alkyl, $C_1$–$C_3$ alkoxy, fluoro and chloro; and (iii) the group represented by graphic formula IIF, wherein A is methylene and D is oxygen, $R_{24}$ is $C_1$–$C_3$ alkyl or $C_1$–$C_3$ alkoxy, $R_{22}$ and $R_{23}$ are each hydrogen or $C_1$–$C_3$ alkyl, and q is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula I having certain of the substituents $R_1$–$R_7$ described hereinbefore, may be prepared by the following Reactions A through F and I through L. Methods for the preparation of compounds represented by graphic formula I wherein $R_5$ is an amino group, are included in Reaction G. Methods for preparing compounds of graphic formula I wherein $R_5$ and $R_6$ together form a heterocyclic ring are included in Reaction H. Reactions M and N describe the preparation of compounds of formula I wherein $R_1$ and/or $R_2$ are amino groups. Reactions O and P describe methods for preparing the compounds of graphic formula I when $R_1$ and $R_2$ come together to form spirocarbocyclic or spiroheterocyclic groups.

Methods for the preparation of compounds wherein $R_1$, $R_2$, B and/or B' is the polyalkoxylated group T are described in U.S. Pat. No. 5,961,892, which disclosure is incorporated herein by reference. Methods for the preparation of compounds wherein $R_1$, $R_2$, B and/or B' is the polymerizable polyalkoxylated group T are described in U.S. application Ser. No. 09/151,911, filed Sep. 11, 1998, which application is incorporated herein by reference.

With reference to the following reactions, compounds represented by graphic formula V, VA, or VB are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B or VB in Reaction C). R and R' represent possible substituents, as described hereinbefore with respect to B and B' of graphic formula I.

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound, e.g., 9-julolidinyl. Propargyl alcohols having a B or B' group represented by graphic formula IIH may be prepared by the methods described in U.S. Pat. No. 5,274,132, column 2, lines 40 to 68.

REACTION B

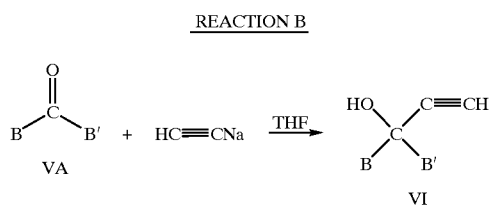

In Reaction C, a substituted benzophenone represented by graphic formula VB is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIII. A mixture of cis and trans half esters forms, which then undergoes cyclodehydration in the presence of acetic anhydride to form a mixture of acetoxynaphthalenes. Further purification to isolate the distinct isomer represented by graphic formula IX may be required. This product is hydrolyzed in an aqueous alcoholic solution of base, such as sodium hydroxide, followed by treatment with aqueous hydrochloric acid (H⁺) to form the carboxynaphthol represented by graphic formula X.

REACTION A

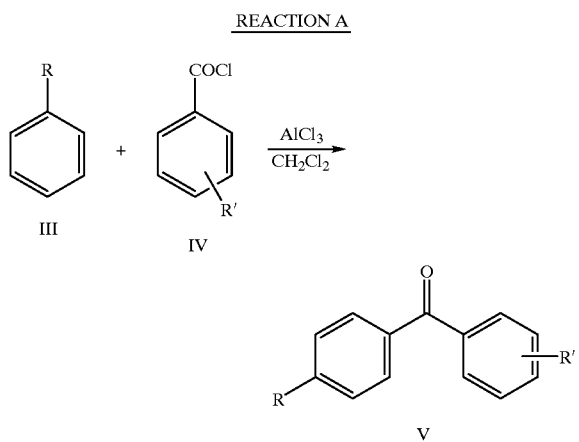

REACTION C

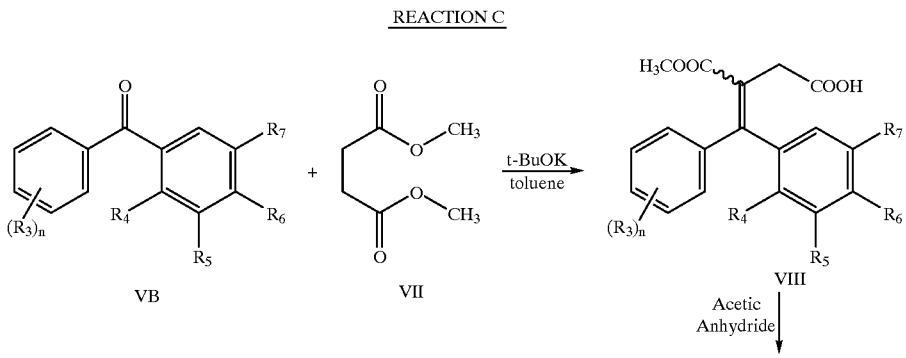

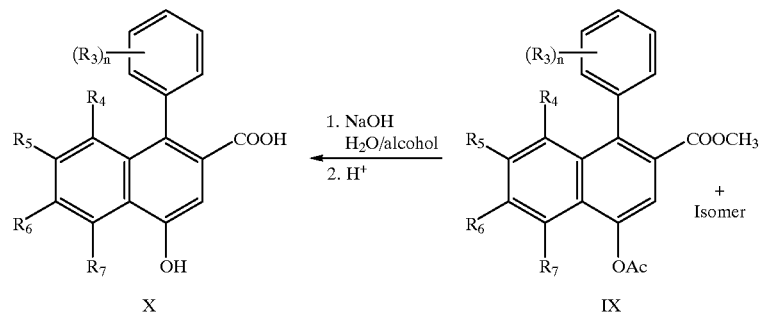

In Reaction D, the carboxynaphthol represented by graphic formula X is cyclized by heating, e.g., from about 110 to about 200° C., in the presence of an acid, such as dodecylbenzene sulfonic acid (DBSA), to a hydroxy-substituted benzo-fused fluorenone represented by graphic formula XI. See the article by F. G. Baddar et al, in the J. Chem. Soc., page 986, 1958.

Coupling of the compound represented by graphic formula XI with a propargyl alcohol represented by graphic formula VI in the presence of a catalytic amount of an acid, e.g., DBSA, results in the indeno-fused naphthopyran represented by graphic formula IA. The reduction of the compound represented by graphic formula XI via a Wolff-Kishner reduction results in the compound represented by graphic formula XIA. Coupling of the compound represented by graphic formula XIA with a propargyl alcohol represented by graphic formula VI results in the indeno-fused naphthopyran represented by graphic formula IB.

REACTION D

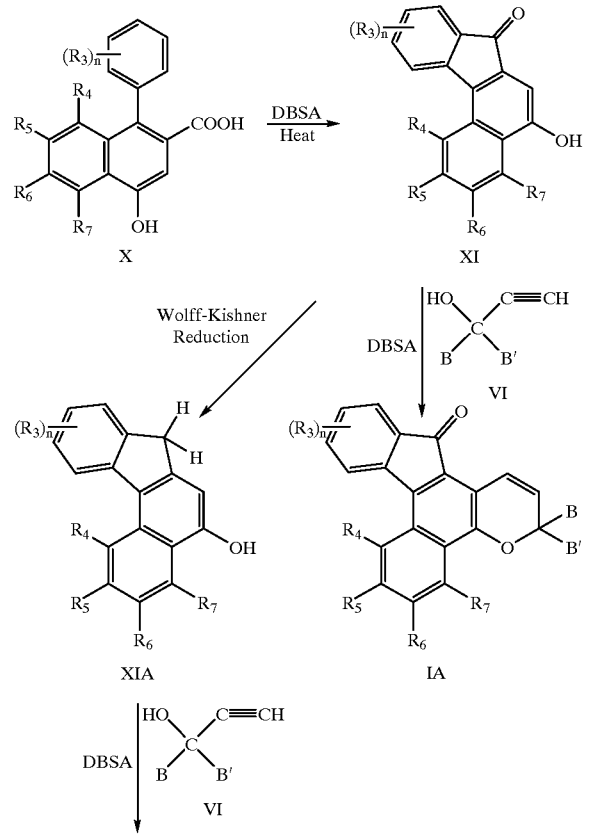

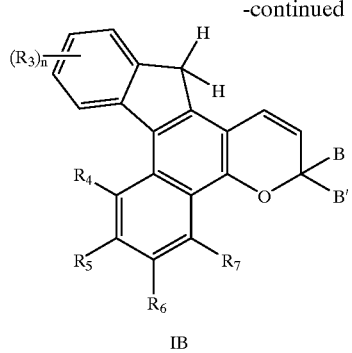

In Reaction E, further methods for preparing compounds represented by graphic formula I having different $R_1$ and $R_2$ substituents are described. Starting with the compound represented by graphic formula IA, reduction with lithium aluminum hydride (LAH) results in the compound represented by graphic formula IC. Other methods for reducing the carbonyl group are described in the text *The Chemistry of the Carbonyl Group*, Chapter 11, Saul Patai, Editor, 1966, Interscience Publishers.

The reaction of the compound represented by graphic formula IC with an acid chloride having a substituent V results in the compound represented by graphic formula ID. Another pathway for incorporating different $R_1$ and $R_2$ substituents on the compound represented by graphic formula IA is by reacting the compound (IA) with a Grignard ($R_1$MgX) or lithium reagent having a substituent $R_1$ to produce the compound represented by graphic formula IE. Subsequent reaction of the compound represented by graphic formula IE with an alcohol having a substituent $R_8$ in the presence of an acid such as hydrochloric acid results in the compound represented by graphic formula IF.

REACTION E

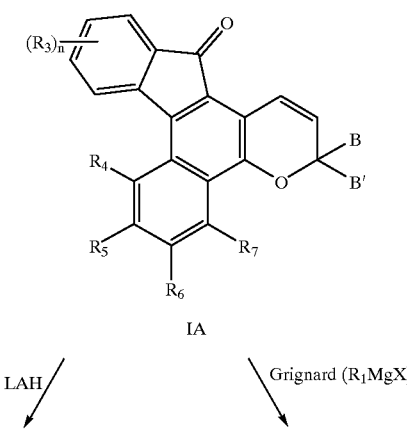

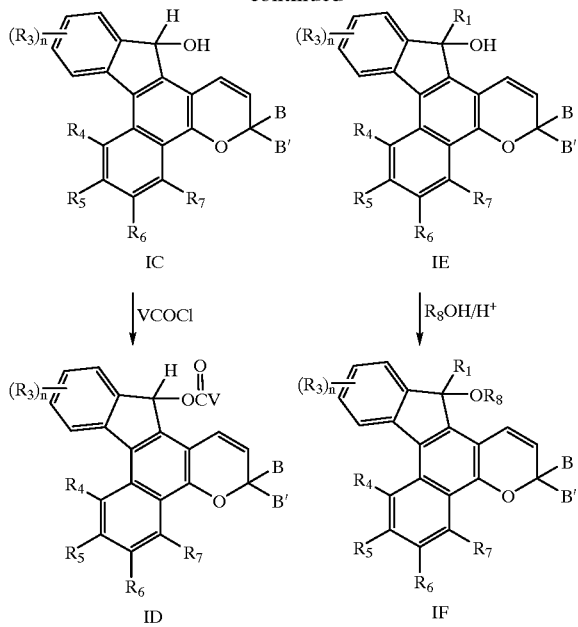

An alternate method of producing compounds of graphic formula I is described in Reaction F. In Reaction F, the acetoxynaphthalene represented by graphic formula IX (from Reaction C) is treated with hydrochloric acid ($H^+$) and methanol to form the carbomethoxy naphthol represented by graphic formula XII. When $R_1$ and $R_2$ are the same, these substituents are introduced by reacting the compound represented by graphic formula XII with a Grignard reagent ($R_1MgX$) followed by heating in the presence of an acid such as DBSA to cyclize the compound yielding a compound represented by graphic formula XIII. Coupling of the compound represented in graphic formula XIII with a propargyl alcohol represented by graphic formula VI results in the indeno-fused naphthopyran represented by graphic formula IG.

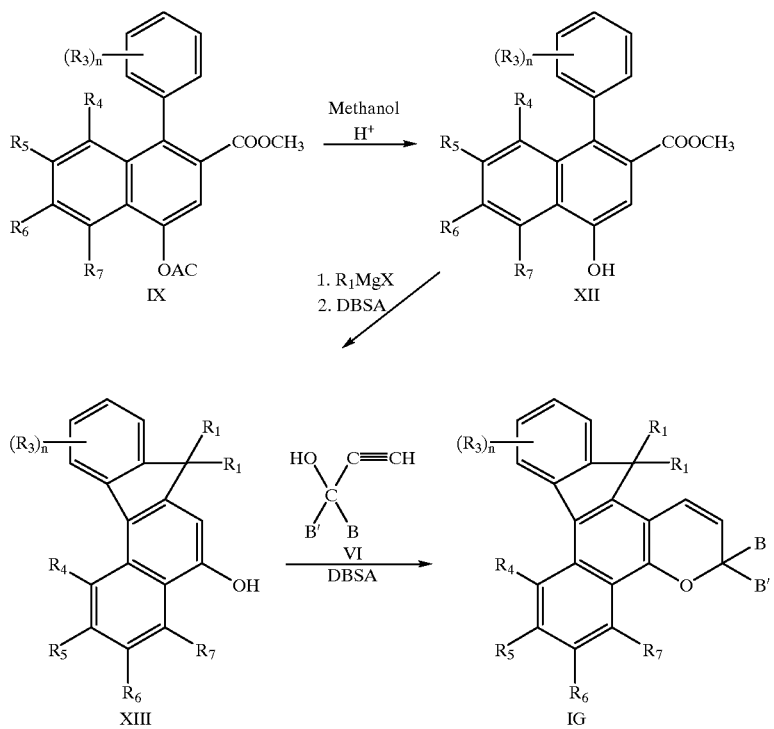

REACTION F

Reaction G along with the procedures described in Reactions C through E are followed to produce amino substituted indeno-fused naphthopyrans.

In Reaction G, the benzophenone represented by graphic formula VC is reacted with a lithium salt of an amine represented by graphic formula XIV in a solvent such as tetrahydrofuran (THF) to produce the amino substituted benzophenone represented by graphic formula XV. As described in Reaction C, treatment of compound XV with dimethyl succinate to produce the corresponding ester, followed by cyclization with acetic anhydride produces an amino substituted acetoxynaphthalene. Methanolysis of the amino substituted acetoxynaphthalene, as described in Reaction C produces the corresponding amino substituted naphthol. The amino substituted naphthol is then coupled with propargyl alcohol as described in Reaction D and may be further modified as described in Reactions E and F to produce amino substituted naphthopyrans.

REACTION G

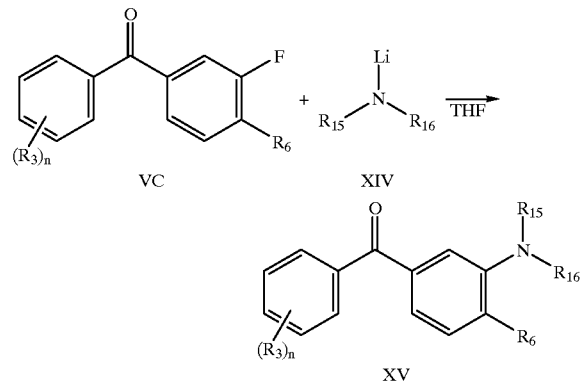

Reaction H along with the procedures described in Reactions C through E may be followed to produce indeno-fused naphthopyrans having a heterocyclic ring fused thereto. In Reaction H, the compounds represented by graphic formulae IIIA and IVA are dissolved in a solvent, such as carbon disulfide or methylene chloride, and reacted in the presence of a Lewis acid, such as aluminum chloride or tin tetrachloride, to form the corresponding substituted benzophenone represented by graphic formula VD. As described in Reaction C, treatment of compound VD with dimethyl succinate to produce the corresponding ester, followed by cyclization with acetic anhydride produces a heterocyclic fused acetoxynaphthalene Methanolysis of the heterocyclic fused acetoxynaphthalene as described in Reaction C produces the corresponding heterocyclic fused naphthol. The naphthol is then coupled with propargyl alcohol, as described in Reaction D, and the product may be further modified as described in Reactions E and F to produce heterocyclic fused naphthopyrans.

REACTION H

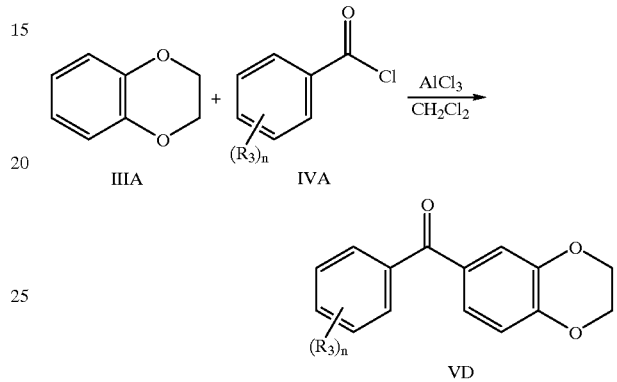

An alternative method of producing the carboxynaphthol of graphic formula X from the half ester of graphic formula VIII (from Reaction C) is presented in Reaction I. Compound VIII is reduced using a Raney alloy ($NiAl_2$) in the presence of aqueous sodium hydroxide to produce the diacid represented by graphic formula XVI. An intramolecular Friedel-Crafts cyclization is carried out by forming the corresponding anhydride, followed by treatment of the anhydride with a Lewis acid, such as aluminum chloride, to provide the keto-acid represented by graphic formula XVII. Aromatization of compound XVII is initiated using basic methanol (MeOH) in the presence of oxygen to yield the naphthoic acid of graphic formula X. Compound X is used as described above in Reactions D and E to produce the indeno-fused naphthols of graphic formula IA through IF.

REACTION I

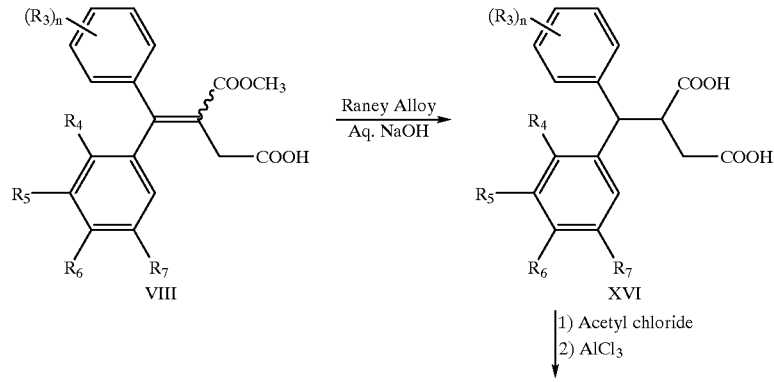

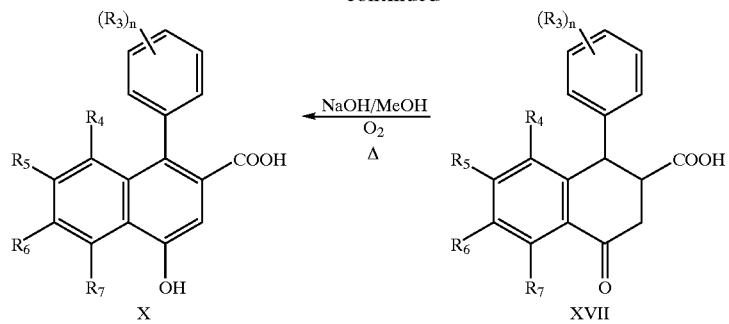

Yet another method of producing the indeno-fused naphthol of graphic formula XI is described in Reaction J. Friedel-Crafts acylation of a substituted benzene represented by graphic formula IVB with succinic anhydride represented by graphic formula XVIII using aluminum chloride yields the compound represented by graphic formula XIX. Esterification of compound XIX yields the compound represented by graphic formula XX. Upon Aldol-type condensation of compound XX with the benzaldehyde represented by graphic formula XXI under basic conditions, such as with sodium methoxide, the enone-acid represented by graphic formula XXII is produced. Cyclization of compound XXII with a Lewis acid such as aluminum chloride followed by hydrolysis yields the indanone represented by graphic formula XXIII. Compound XXIII is converted to the compound represented by graphic formula XXIV by treatment with oxalyl chloride $(COCl)_2$ followed by cyclization using a Lewis acid such as stannous chloride or both steps can be replaced by acid promoted cyclization using phosphoric acid. Compound XXIV is oxidized using methanolic sodium hydroxide with oxygen sparging to produce the indeno-fused naphthol of graphic formula XI. This reaction mechanism is further described by C. F. Koelsch in the Journal of Organic Chemistry, volume 26, page 2590, 1961.

REACTION J

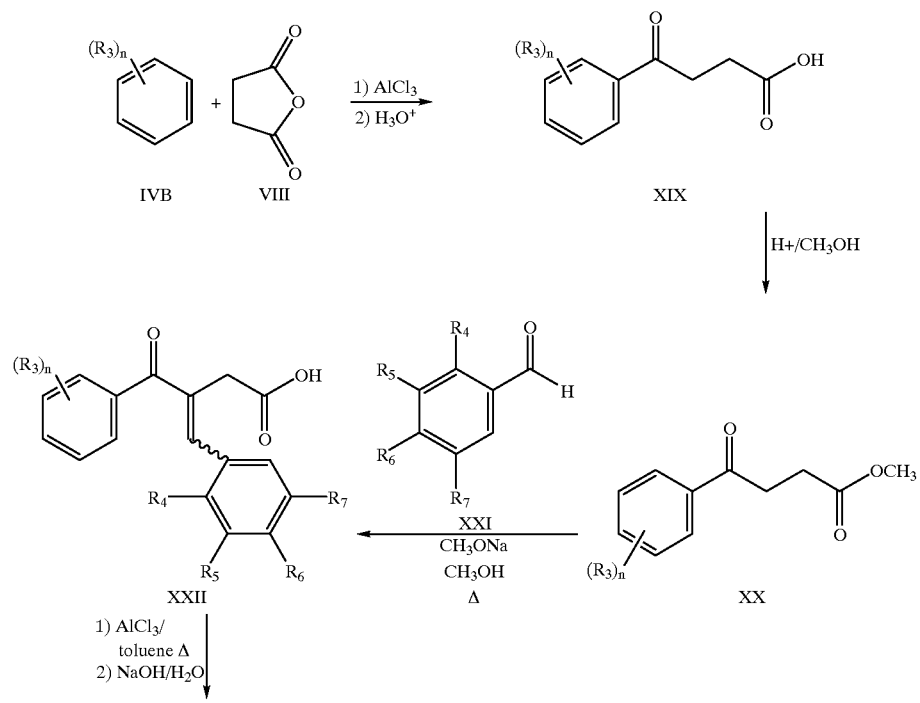

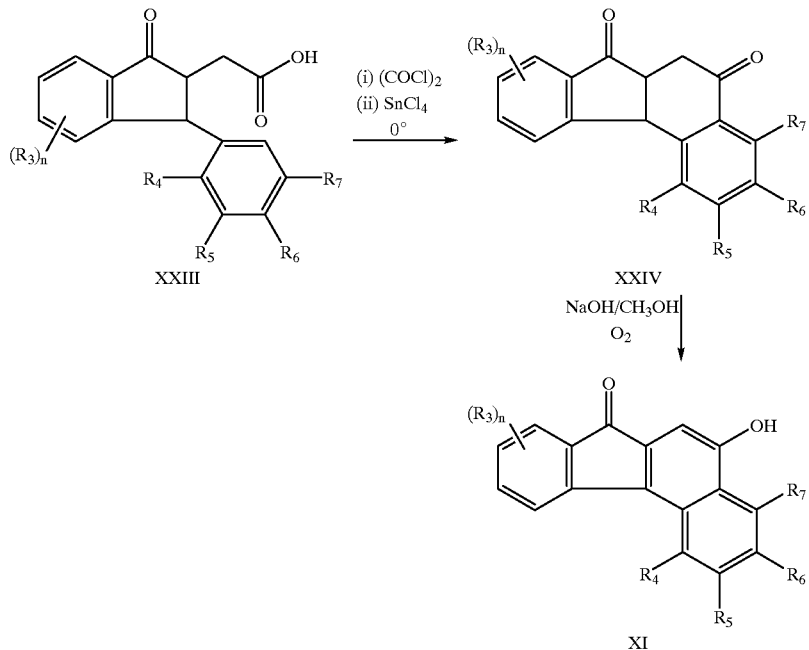

In Reaction K, the substituted ketoester represented 5 by graphic formula XXV and an aryl aldehyde represented by graphic formula XXVI are treated with a base, such as sodium methoxide, under conditions of an Aldol-type condensation to produce the substituted 3-keto-4-aryl-3-butenoic acid represented by graphic formula XXVII. $R_1'$ may represent an aromatic substituent or a non-aromatic substituent. The substituted 3-keto-4-aryl-3-butenoic acid represented by graphic formula XXVII is treated with acetic anhydride to produce the substituted 3-keto-1-acetoxynaphthalene represented by graphic formula XXVIII. The acetate group of this compound is removed under conditions of basic or acidic hydrolysis to yield the substituted 3-keto-1-hydroxynaphthalene represented by graphic formula XXIX. Addition of an excess of nucleophile, e.g., Grignard reagents, lithium reagents or cyanide anion, produces the compound represented by graphic formula XXX. $R_2'$ may represent an aromatic substituent or a non-aromatic substituent provided that either $R_1'$ or $R_2'$ or both $R_1^1$ and $R_2'$ are aromatic substituents, preferably phenyl. Compound XXX is a tertiary alcohol or, in the case when hydride is used as the nucleophile, a secondary alcohol.

REACTION K

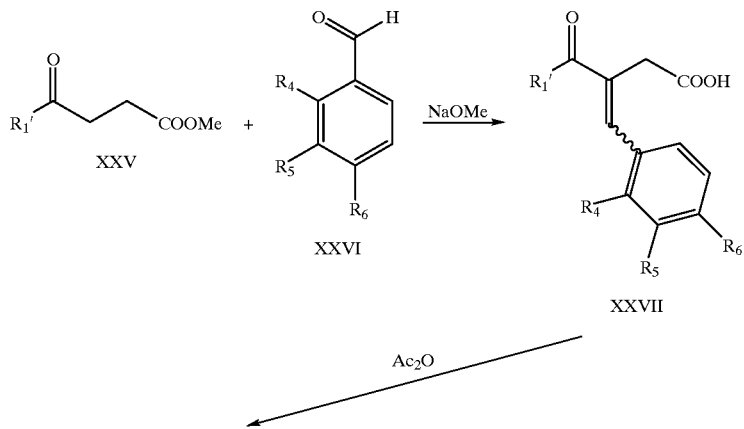

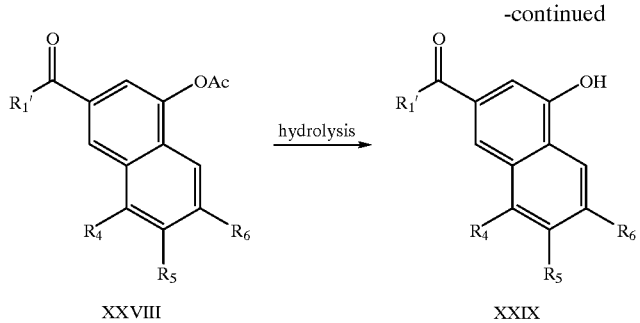

XXVIII   XXIX   XXX

In Reaction L the compound represented by the graphic formula XXXA is subjected to dehydration under acidic conditions as described by S. Patai and S. Dayagi, J.Chem. Soc, 1962, pp. 716–723; and G. Chuchani, J. Chem. Soc., 1959, pp. 1753–1756; to yield the indeno-fused naphthol represented by graphic formula XXXI. The indeno-fused naphthol XXXI can be further modified by replacing the hydrogen adjacent to $R_2$ with hydroxy or alkoxy group via oxidation. The resulting naphthol XXXII can be used to produce the indeno-fused naphthopyrans of graphic formula I (where either $R_1$ or $R_2$ is a hydroxy or an alkoxy group) by the steps previously described for coupling with propargyl alcohol in Reaction D. Naphthol XXXI can be used to produce the indeno-fused naphthopyrans of graphic formula I wherein one or both substituents $R_1$ and $R_2$ are hydrogen by the steps previously described for coupling with propargyl alcohol in Reaction D. Indeno-fused naphthopyrans of graphic formula I having either $R_1$ or $R_2$, or both $R_1$ and $R_2$ as hydrogen can be further modified by replacing the hydrogen adjacent to $R_2$ with an alkyl group via alkylation with alkyl halides under basic conditions to yield indeno-fused naphthopyrans I where either $R_1$ or $R_2$, or both $R_1$ and $R_2$ are alkyl groups.

REACTION L

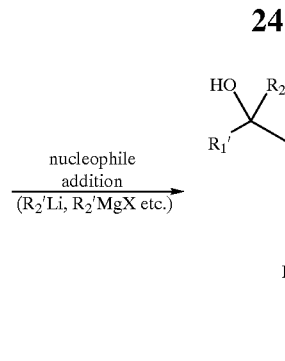

XXXII

Reaction M or N may be followed to produce indeno-fused naphthopyrans where $R_1$ and/or $R_2$ are an amine group. In Reaction M, the compound represented by graphic formula XI from Reaction D is coupled with a primary aliphatic amine ($H_2NAlk$) or primary aromatic amine ($H_2NAr$), with the aliphatic amino shown below by example, under dehydrating conditions either azeotropically by distillation or with a drying agent such as titanium tetrachloride yielding the corresponding fluorenimine represented by graphic formula XXXIII. Compound XXXIII may be reduced using sodium borohydride to produce the corresponding amino fluorene represented by graphic formula XXXIVA. Compound XXXIII may also be reductively alkylated using an organolithium compound Alk—Li or Ar—Li or a Grignard reagent to yield the compounds represented by graphic formulae XXXIVB and XXXIVC. When the primary aliphatic amino ($H_2NAlk$) is benzylamino, treatment of compound XXXIII (having a benzyl substituent as Alk) with a base, such as sodium hydride, and a chloroformate derivative, such as ClC(O)W (wherein W is certain of the substituents described hereinbefore), yields the corresponding amino ester represented by graphic formula XXXIVD.

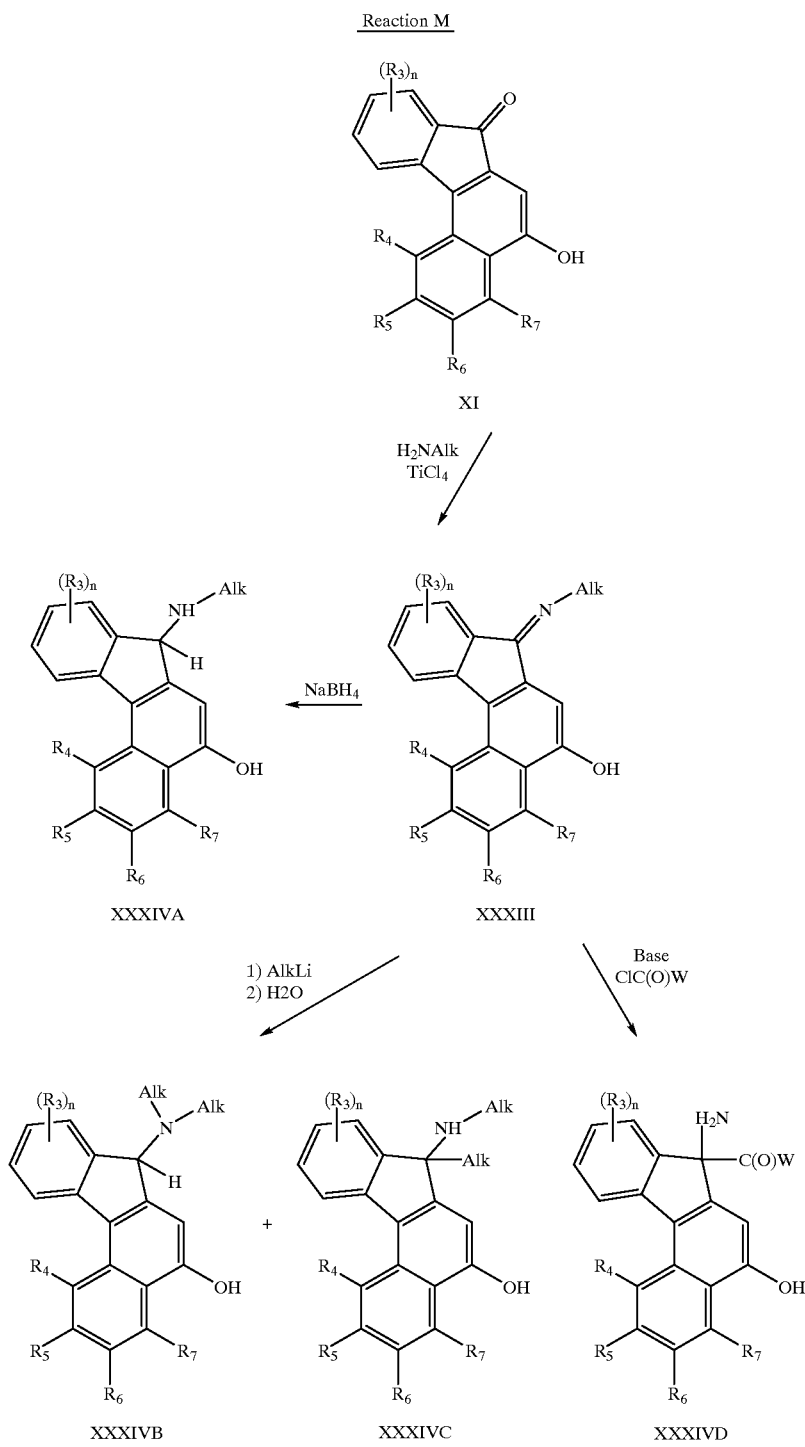

In Reaction N, the compound represented by graphic formula XI is treated with a secondary amine, e.g. dialiphatic amine (HN(Alk)$_2$), a diaromatic amine (HN(Ar)$_2$) or an aliphatic aromatic amine (HNAlkAr), to produce the corresponding hemiaminal represented by graphic formula XXXV. Upon addition of excess of the amino, such as HN(Alk)$_2$, the aminal represented by graphic formula XXX-IVE is formed. Coupling of each of compounds XXXIVA through XXXIVE with propargyl alcohol as described in Reaction D results in the corresponding indeno-fused naphthopyrans. Alternatively, the oxo substituted indeno-fused naphthopyran represented by graphic formula IA (Reaction D) may be treated as described in Reactions M and N via amination and reductive amination to produce indeno-fused naphthopyrans having amino groups at the $R_1$ and/or $R_2$ substituents.

REACTION N

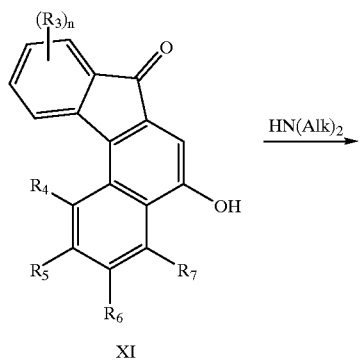

XI

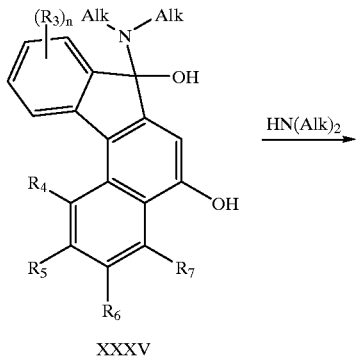

XXXV

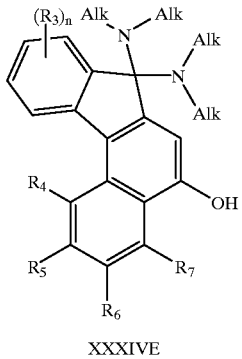

XXXIVE

In Reaction O, the indeno-fused naphthopyran represented by graphic formula IA is first reacted with compound XXXVI and then cyclized under acidic conditions ($H^+$) to produce the compound represented by graphic formula IH. Substituents $R_{22}$ and $R_{23}$ are the same as previously described.

REACTION O

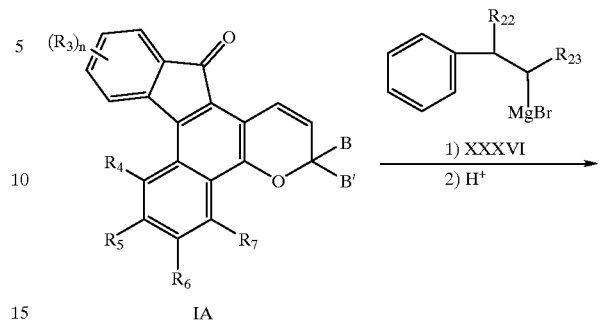

IA

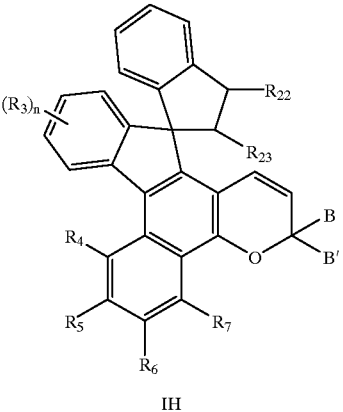

IH

In Reaction P, the indeno-fused naphthopyran represented by graphic formula IA is first reacted with compound XXXVII and then cyclized under acidic conditions ($H^+$) to produce the compound represented by graphic formula IJ. E in compound XXXVII may be selected from the groups, (—O—), (—$CH_2$—), and (—CH=CH—) and s is an integer of from 0 to 2. When E is (—$CH_2$—), s equals 1–2, when E is (—CH=CH—), s equals 1 and when s equals 0, E is a carbon-carbon bond.

REACTION P

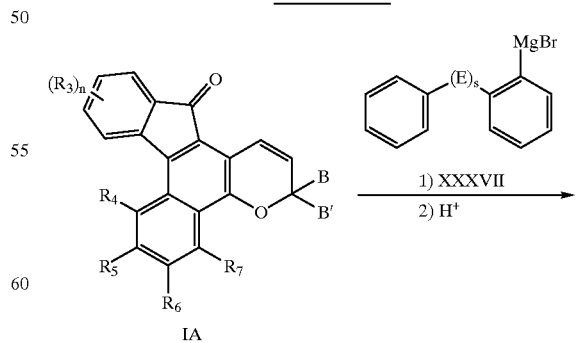

IA

-continued

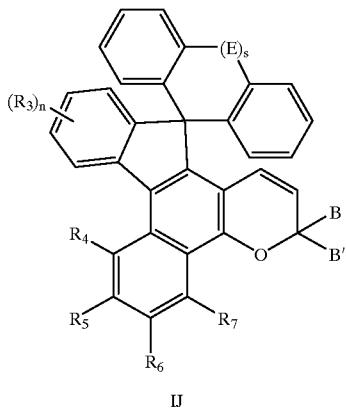

IJ

Compounds represented by graphic formula I may be used in those applications in which organic photochromic substances may be employed, such as optical lenses, e.g., vision correcting ophthalmic lenses, plano lenses and contact lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit blended color changes from colorless to colors of gray, brown or green. These blended color changes are a result of one absorption band (Band "A") in the 420–500 nm region and another absorption band (Band "B") in the 500–650 nm region.

Examples of contemplated naphthopyran compounds within the scope of the invention are the following:

(a) 3,3-di(4-methoxyphenyl)-6,7,10,11-tetramethoxy-13, 13-dimethyl-3H,13H-indeno[2,1-f]naphtho[1,2-b] pyran;

(b) 3-phenyl-3-(4-morpholinophenyl)-6,7,10,11-tetramethoxy-13,13-dimethyl-3H,13H-indeno[2,1-f] naphtho[1,2-b]pyran;

(c) 3,3-di(4-methoxyphenyl)-6,7,10,11-tetramethoxy-13-hydroxy-13-ethyl-3H,13H-indeno[2,1-f]naphtho[1,2-b]pyran;

(d) 3,3-di(4-methoxyphenyl)-6,7-dimethoxy-13,13-dimethyl-3H,13H-indeno[2,1-f]naphtho[1,2-b]pyran;

(e) 3,3-di(4-methoxyphenyl)-6,7-dimethoxy-13-hydroxy-13-ethyl-3H,13H-indeno[2,1-f]naphtho[1,2-b]pyran;

(f) 3,3-di(4-methoxyphenyl)-6,7,10,11-tetramethoxy-13, 13-diethyl-3H,13H-indeno[2,1-f]naphtho[1,2-b]pyran;

(g) 3,3-di(4-methoxyphenyl)-6,7-dimethoxy-13-phenyl-3H,13H-indeno[2,1-f]naphtho[1,2-b]pyran;

(h) 3-(4-methoxyphenyl)-3-(4-morpholinophenyl)-6,7-dimethoxy-13-phenyl-3H,13H-indeno[2,1-f]naphtho[1,2-b]pyran;

(i) 3-(4-methoxyphenyl)-3-(4-morpholinophenyl)-6,7-dimethoxy-13,13-dimethyl-3H,13H-indeno[2,1-f]naphtho[1,2-b]pyran;

(j) 3-(4-methoxyphenyl)-3-(4-dimethylaminophenyl)-6, 7-dimethoxy-13,13-dimethyl-3H,13H-indeno[2,1-f]naphtho[1,2-b]pyran;

(k) 3,3-di(4-methoxyphenyl)-6,7,8-trimethoxy-13-phenyl-3H,13H-indeno[2,1-f]naphtho[1,2-b]pyran;

(l) 3-(4-methoxyphenyl)-3-(4-morpholinophenyl)-6,7,10, 11-tetramethoxy-13-hydroxy-13-ethyl-3H,13H-indeno[2,1-f]naphtho[1,2-b]pyran;

(m) 3-(4-methoxyphenyl)-3-(4-morpholinophenyl)-6,7, 10,11-tetramethoxy-13-hydroxy-13-butyl-3H,13H-indeno[2,1-f]naphtho[1,2-b]pyran;

(n) 3-(4-morpholinophenyl)-3-phenyl-6,7-dimethoxy-13-hydroxy-13-ethyl-3H,13H-indeno[2,1,-f]naphtho[1,2-b]pyran;

(o) 3,3-di(4-methoxyphenyl)-6,7-dimethoxy-13-hydroxy-13-butyl-3H,13H-indeno[2,1,-f]naphtho[1,2-b]pyran;

(p) 3-(4-morpholinophenyl)-3-phenyl-6,7-dimethoxy-13-hydroxy-13-butyl-3H,13H-indeno[2,1,-f]naphtho[1,2-b]pyran;

(q) 3-(4-methoxyphenyl)-3-(4-morpholinophenyl)-6,7-dimethoxy-13-hydroxy-13-ethyl-3H,13H-indeno[2,1-f]naphtho[1,2-b]pyran;

(r) 3-(4-methoxyphenyl)-3-(4-morpholinophenyl)-6,7-dimethoxy-13-ethyl-13-methoxy-3H,13H-indeno[2,1-f]naphtho[1,2-b]pyran;

(s) 3-(4-methoxyphenyl)-3-(4-morpholinophenyl)-6,7-dimethoxy-13-hydroxy-13-methyl-3H,13H-indeno[2, 1-f]naphtho[1,2-b]pyran; and (t) 3-(4-methoxyphenyl)-3-(4-morpholinophenyl)-6,7-dimethoxy-13-methoxy-13-methyl-3H,13H-indeno[2, 1-f]naphtho[1,2-b]pyran.

Other than in the operating examples, or where otherwise indicated, all numbers expressing wavelengths, quantities of ingredients or reaction conditions used herein are to be understood as modified in all instances by the term "about".

It is contemplated that the photochromic naphthopyrans of the present invention may each be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing the same, and may be incorporated, e.g., dissolved or dispersed, in a polymeric organic host material used to prepare photochromic articles which color when activated to an appropriate hue.

Examples of complementary organic photochromic compounds include other naphthopyrans and indenonaphthopyrans, chromenes and oxazines, substituted 2H-phenanthro[4,3-b]pyran and 3H-phenanthro[1,2-b]pyran compounds, benzopyran compounds having substituents at the 2-position of the pyran ring and mixtures of such photochromic compounds. Such photochromic compounds are described in U.S. Pat. Nos. 3,562,172; 3,567,605; 3,578, 602; 4,215,010; 4,342,668; 4,816,584; 4,818,096; 4,826, 977; 4,880,667; 4,931,219; 5,066,818; 5,238,981; 5,274, 132; 5,384,077; 5,405,958; 5,429,774; 5,458,814; 5,466, 398; 5,514,817; 5,552,090; 5,552,091; 5,565,147; 5,573, 712; 5,578,252; 5,637,262; 5,645,767; 5,656,206; 5,658, 500; 5,658,501; 5,674,432 and 5,698,141. Spiro(indoline) pyrans are also described in the text, *Techniques in Chemistry*, Volume III, "Photochromism", Chapter 3, Glenn H. Brown, Editor, John Wiley and Sons, Inc., New York, 1971.

The complementary organic photochromic materials may also include polymerizable photochromic compounds, such as those disclosed in U.S. Pat. Nos. 4,719,296; 5,166,345; 5,236,958; 5,252,742; 5,359,035; and 5,488,119.

Other complementary photochromic substances contemplated are metal-dithiozonates, e.g., mercury dithizonates which are described in, for example, U.S. Pat. No. 3,361,706; and fulgides and fulgimides, e.g., the 3-furyl and 3-thienyl fulgides and fulgimides, which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

The photochromic compounds of the present invention may be associated with a polymeric organic host material or other substrate by various means. They may be incorporated, i.e., dissolved and/or dispersed, into the host material, polymerized with other components of the host material, and/or incorporated into a coating applied to a substrate, e.g., a polymeric coating applied to one surface of the polymeric organic host material.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of the photochromic naphthopyrans to be applied to or incorporated into a coating composition or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, the ultimate color desired and the method of application to the host material or substrate. Generally, the amount of total photochromic compound incorporated into or applied to a photochromic optical host material may range from about 0.05 to about 2.0, e.g., from 0.2 to about 1.0, milligrams per square centimeter of surface to which the photochromic compound is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872, the disclosure of which is incorporated herein by reference.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029, which is incorporated herein by reference. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays. A preferred coating composition is polyurethane prepared from organic polyol(s) and an isocyanate. The photochromic substances of the present invention may be dissolved or dispersed within the organic polyol component or isocyanate component of the polyurethane coating or may be added to a mixture of the polyurethane-forming components.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as piano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, mono- or polyfunctional, e.g., di- or multi-functional, acrylate and/or methacrylate monomers, poly($C_1$–$C_{12}$ alkyl methacrylates), such as poly(methyl methacrylate), poly(oxyalkylene)dimethacrylate, poly(alkoxylated phenol methacrylates), cellulose acetate, cellulose triacetate, cellulose acetate propionate, cellulose acetate butyrate, poly(vinyl acetate), poly(vinyl alcohol), polyvinyl chloride), poly(vinylidene chloride), polyurethanes, polythiourethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No.

5,753,146, column 8, line 62 to column 10, line 34, which disclosure is incorporated herein by reference.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic naphthopyrans of the present invention with optical organic resin monomers used to produce optically clear coatings and polymerizates, i.e., materials suitable for optical applications, such as for example plano, contact and ophthalmic lenses, windows, and automotive transparencies. Such optically clear polymerizates may have a refractive index that may range from about 1.48 to about 1.75, e.g., from about 1.495 to about 1.66.

Specifically contemplated are polymerizates of optical resins sold by PPG Industries, Inc. under the CR-designation, e.g., CR-307 and CR-407, and polymerizates prepared for use as hard or soft contact lenses. Methods for producing both types of contact lenses are disclosed in U.S. Pat. No. 5,166,345, column 11, line 52, to column 12, line 52, which disclosure is incorporated herein by reference. Additional polymerizates contemplated for use with the photochromic polyalkoxylated naphthopyrans of the present invention are polymerizates used to form soft contact lenses with high moisture content described in U.S. Pat. No. 5,965,630 and extended wear contact lenses described in U.S. Pat. No. 5,965,631, both disclosures of which are incorporated herein by reference.

The present invention is more particularly described in the following examples which are intended as illustrative only, since numerous modifications and variations therein will be apparent to those skilled in the art.

EXAMPLE 1

Step 1

1,2-Dimethoxybenzene (74.5 grams) and a solution of 3,4-dimethoxybenzoyl chloride (98.2 grams) in 500 milliliters (mL) of methylene chloride were added to a reaction flask fitted with a solid addition funnel under a nitrogen atmosphere. Solid anhydrous aluminum chloride (71.8 grams) was added to the reaction mixture with occasionally cooling of the reaction mixture in an ice/water bath. The reaction mixture was stirred at room temperature for 3 hours. The resulting mixture was poured into 300 mL of a 1:1 mixture of ice and 1N hydrochloric acid and stirred vigorously for 15 minutes. The mixture was extracted twice with 100 mL methylene chloride. The organic layers were combined and washed with 50 mL of 10 weight percent sodium hydroxide followed by 50 mL of water. The methylene chloride solvent was removed by rotary evaporation to give a yellow solid. Recrystallization from 95 percent ethanol yielded 127 grams of beige needles having a melting point of 146–147° C. A nuclear magnetic resonance (NMR) spectrum showed the product to have a structure consistent with 3,3',4,4'-tetramethoxybenzophenone.

Step 2

Potassium t-butoxide (55.4 grams) and 100.0 grams of the product from Step 1 were added to a reaction flask containing 600 mL of toluene under a nitrogen atmosphere. The mixture was heated to reflux and dimethyl succinate (193 grams) was added dropwise over a 1 hour period. The mixture was refluxed for 5 hours and cooled to room temperature. The resulting precipitate was collected by vacuum filtration and washed with fresh toluene to yield 143 grams of a beige powder. The powder was dissolved in about 200 mL of water and acidified to pH 2 with 4N hydrochloric acid. The acidic solution was extracted five times with 50 mL of methylene chloride. The organic extracts were combined and concentrated by rotary evaporation to produce 102 grams of a thick brown oil. An NMR spectrum showed the desired product to have a structure consistent with 4,4-di(3, 4-dimethoxyphenyl)-3-methoxycarbonyl-3-butenoic acid. This material was not purified further but was used directly in the next step.

Step 3

The crude half-ester from Step 2 (100 grams), 60 mL of acetic anhydride, and 300 mL of toluene were added to a reaction flask under a nitrogen atmosphere. The reaction mixture was heated to 110° C. for 6 hours and cooled to room temperature, and the solvents (toluene and acetic anhydride) were removed by rotary evaporation. The residue was dissolved in 300 mL of methylene chloride and 200 mL of water. Solid sodium carbonate was added to the biphasic mixture until bubbling ceased. The layers separated and the aqueous layer was extracted with two 50 mL portions of methylene chloride. The organic layers were combined and the solvent (methylene chloride) was removed by rotary evaporation to yield a thick red oil. The oil was dissolved in warm methanol and chilled at 0° C. for 2 hours. The resulting crystals were collected by vacuum filtration, washed with cold methanol to produce 38.9 grams of a product having a melting point of 176–177° C. An NMR spectrum showed the product to have a structure consistent with 1-(3,4-dimethoxyphenyl)-2-methoxycarbonyl-4-acetoxy-6,7-dimethoxynaphthalene.

Step 4

1-(3,4-Dimethoxyphenyl)-2-methoxycarbonyl-4-acetoxy-6,7-dimethoxynaphthalene from Step 3 (5 grams), 5 mL of 12M hydrochloric acid, and 30 mL of methanol were combined in a reaction flask and heated to reflux for 1 hour.

The reaction mixture was cooled and the resulting precipitate was collected by vacuum filtration and washed with cold methanol yielding 2.1 grams of beige needles having a melting point of 213–214° C. An NMR spectrum showed the product to have structure consistent with 1-(3,4-dimethoxyphenyl)-2-methoxycarbonyl-4-hydroxy-6,7-dimethoxynaphthalene.

Step 5

A reaction flask was charged with 1-(3,4-dimethoxyphenyl)-2-methoxycarbonyl-4-hydroxy-6,7-dimethoxynaphthalene from Step 4 (0.9 grams) under a nitrogen atmosphere. Anhydrous tetrahydrofuran (20 mL) was added to the flask. The reaction mixture was cooled in a dry ice/acetone bath and 9 mL of a methyl magnesium chloride solution (1M in tetrahydrofuran) was added dropwise over 15 minutes. The resulting yellow reaction mixture was stirred at 0° C. for 2 hours and slowly warmed to room temperature. The reaction mixture was poured into 50 mL of an ice/water mixture. Ether (20 mL) was added, and the layers separated. The aqueous layer was extracted with two 20 mL portions of ether, and the organic portions were combined and washed with 30 mL of water. The organic layer was dried over anhydrous magnesium sulfate and concentrated by rotary evaporation. The resulting oil was transferred into a reaction vessel (fitted with a Dean-Stark trap) containing 50 mL of toluene to which two drops of dodecylbenzene sulfonic acid were added. The reaction mixture was heated to reflux for 2 hours and cooled. The toluene was removed via rotary evaporation to yield 0.73 grams of a dark brown solid. An NMR spectrum showed the product to have a structure consistent with 7,7-dimethyl-5-hydroxy-2,3,9,10-tetramethoxy-7H-benzo[c]fluorene. This material was not purified further but was used directly in the next step.

Step 6

7,7-Dimethyl-5-hydroxy-2,3,9,10-tetramethoxy-7H-benzo[C]fluorene from Step 5 (450 milligrams), 1,1-di(4-methoxyphenyl)-2-propyn-1-ol (345 milligrams), two drops of dodecylbenzene sulfonic acid and 15 mL of toluene were combined in a reaction vessel and stirred at ambient temperature for three and one half hours. The reaction mixture was diluted with 15 mL of toluene and 15 mL of water. The organic layer was separated, dried over sodium sulfate, and concentrated by rotary evaporation. The residue was chromatographed on a silica gel using chloroform as the elutant. Photochromic fractions were collected, concentrated by rotary evaporation and the resulting solid was recrystallized from diethyl ether yielding 289 milligrams of needles having a melting point of 213–214° C. An NMR spectrum showed the product to have a structure consistent with 3,3-di(4-methoxyphenyl)-6,7,10,11-tetramethoxy-13,13-dimethyl-3H,13H-indeno[2,1-f]naphtho[1,2-b]pyran.

EXAMPLE 2

The process of Example 1 was followed except that in Step 6, 1-(4-morpholinophenyl)-1-phenyl-2-propyn-1-ol was used in place of 1,1-di(4-dimethoxyphenyl)-2-propyn-1-ol. The resulting product was chromatographed on silica gel using ethyl acetate:hexane (1:1 v/v) as the elutant. The desired product was recrystallized from hot ethanol (95%) to yield 239 milligrams of a product having a melting point of 195–197° C. An NMR spectrum showed the product to have a structure consistent with 3-phenyl-3-(4-morpholinophenyl)-6,7,10,11-tetramethoxy-13,13-dimethyl-3H,13H-indeno[2,1-f]naphtho[1,2-b]pyran.

EXAMPLE 3

Step 1

The process of Example 1 was followed except that the 1-(3,4-dimethoxyphenyl)-2-methoxycarbonyl-4-acetoxy-6,7-dimethoxynaphthalene produced in Step 3 (20.0 grams) was added to a reaction flask containing 150 mL of a 10 weight percent aqueous sodium hydroxide solution and 15 mL of methanol. The mixture was refluxed for 3 hours and cooled. The aqueous layer was washed twice with methylene chloride, 50 mL each, and the combined organic layers were extracted with 100 mL of water. The aqueous layers were combined and acidified to pH 2 with an aqueous solution of 6N hydrochloric acid. The aqueous layer was extracted four times with 50 mL portions of methylene chloride. The methylene chloride layers were combined and concentrated by rotary evaporation. The resulting oil was crystallized from ethanol (95%) to yield 12.0 grams of a beige powder having a melting point of 223–224° C. An NMR spectrum showed the product to have a structure consistent with 1-(3,4-dimethoxyphenyl)-4-hydroxy-6,7-dimethoxy-2-naphthoic acid.

Step 2

1-(3,4-Dimethoxyphenyl)-4-hydroxy-6,7-dimethoxy-2-naphthoic acid from Step 1 (6.0 grams), 100 mL of toluene and 20 milligrams of dodecylbenzene sulfonic acid were added to a reaction flask fitted with a Dean-Stark trap. The resulting mixture was heated to reflux for 5 hours. A deep red solid precipitate formed. Two more portions of dodecylbenzene sulfonic acid (50 milligrams and 500 milligrams) were added to the refluxing mixture at 3 hour intervals. The mixture was cooled and the solid was collected by vacuum filtration. Any unreacted starting material was removed via digestion in boiling acetonitrile. The mixture was vacuum filtered to yield 4.45 grams of a product having a melting point range of 283–288° C. An NMR spectrum showed the product to have a structure consistent with 2,3,9,10-tetramethoxy-5-hydroxy-7H-benzo[C]fluoren-7-one.

Step 3

2,3,9,10-Tetramethoxy-5-hydroxy-7H-benzo[C]-fluoren-7-one from Step 2 (2.19 grams) was added to a reaction flask containing 1,1-di(4-methoxyphenyl)-2-propyn-1-ol (1.81 grams) and 75 mL of chloroform and stirred at room temperature. Dodecylbenzene sulfonic acid (10 milligrams) was added and the reaction mixture immediately darkened. After stirring for one and one half hours, the chloroform was removed by rotary evaporation. The residue was dissolved in warm acetone and crystals formed upon cooling to 0° C. Red colored needles (3.2 grams) having a melting point range of 249–254° C. were collected by vacuum filtration. An NMR spectrum showed the product to have a structure consistent with 3,3-di(4-methoxyphenyl)-6,7,10,11-tetramethoxy-13-oxo-3H,13H-indeno[2,1-f]naphtho[1,2-b]pyran.

Step 4

3,3-Di(4-methoxyphenyl)-6,7,10,11-tetramethoxy-13-oxo-3H,13H-indeno[2,1-f]naphtho[1,2-b]pyran from Step 3 (3.0 grams) was added to a dry reaction flask under a nitrogen atmosphere. Anhydrous tetrahydrofuran (50 mL) was added and the reaction mixture was cooled in a dry ice/acetone bath. Ethyl magnesium chloride (7.2 mL of a 2M tetrahydrofuran solution) was added dropwise over a one hour period, and the reaction was slowly warmed to room temperature. The reaction mixture was poured into a flask containing 100 grams of ice, and this mixture was acidified to pH 3 with a 6N solution of hydrochloric acid. The layers were separated and the aqueous layer was extracted four times with 50 mL portions of diethyl ether. The organic layers were combined and the solvents (ether and tetrahydrofuran) were removed by rotary evaporation. The residue was chromatographed on silica gel using a 3:1 v/v mixture of hexane and ethyl acetate as the elutant. The photochromic fractions were collected, concentrated by rotary evaporation and recrystallized from ethanol (95%) yielding 1.29 grams of the desired product. An NMR spectrum showed the product to have a structure consistent with 3,3-di(4-methoxyphenyl)-6,7,10,11-tetramethoxy-13-hydroxy-13-ethyl-3H,13H-indeno[2,1-f]naphtho[1,2-b]pyran.

EXAMPLE 4

Step 1

The process of Step 1 of Example 1 was followed except that 92.5 grams of 1,2-dimethoxy benzene and 89.7 grams of aluminum chloride were used. Benzoyl chloride (84.3 grams) was used instead of 3,4-dimethoxy benzoyl chloride to yield 147 grams of a product having a melting point of 103–105° C. An NMR spectrum showed the product to have a structure consistent with 3,4-dimethoxy benzophenone.

Step 2

The process of Step 2 of Example 1 was followed except that 3,4-dimethoxybenzophenone (90 grams) was used in place of 3,3'4,4'-tetramethoxybenzophenone, and 144.8 grams of dimethyl succinate (dissolved in 300 mL of toluene), 62 grams of potassium t-butoxide, and 700 mL of toluene were used. Instead of isolating the precipitate, 300 mL of water was added to the reaction mixture and vigorously stirred for 20 minutes. The aqueous and organic phases separated and the organic phase was extracted with 100 mL portions of water three times. The combined aqueous layers were washed with 50 mL portions of chloroform three times. The aqueous layer was acidified to pH 2 with 6N hydrochloric acid and a precipitate formed. The aqueous layer was extracted with three 100 mL portions of chloroform. The organic extracts were combined and concentrated by rotary evaporation. An NMR spectrum of the resulting oil showed the product to have structures consistent with a mixture of (E and Z) 4-(3,4-dimethoxyphenyl)-4-phenyl-3-methoxycarbonyl-3-butenoic acids.

Step 3

The process of Example 1, Step 3, was followed using the oil containing (E and Z) 4-(3,4-dimethoxyphenyl)-4-phenyl-3-methoxycarbonyl-3-butenoic acids (8.6 grams) from Step 2, which was added to a reaction flask containing acetic anhydride (5 mL) and toluene (50 mL) An NMR spectrum showed the recovered solid product to have structures consistent with a mixture of 1-(3,4-dimethoxyphenyl)-2-methoxycarbonyl-4-acetoxynaphthalene and 1-phenyl-2-methoxycarbonyl-4-acetoxy-6,7-dimethoxynaphthalene. The product mixture was used without further purification in subsequent reactions.

Step 4

The process of Example 1, Step 4 was followed except that the mixture of 1-(3,4-dimethoxyphenyl)-2-methoxycarbonyl-4-acetoxynaphthalene and 1-phenyl-2-methoxycarbonyl-4-acetoxy-6,7-dimethoxynaphthalene from Step 3 was used. The product was purified by filtering through a plug of silica gel using a 2:1 mixture of hexane and ethyl acetate as the elutant. Concentration of the filtrate by rotary evaporation yielded 3.3 grams of a beige solid. An NMR spectrum showed the product to have structures consistent with a mixture of 1-(3,4-dimethoxyphenyl)-2-methoxycarbonyl-4-hydroxynaphthalene and 1-phenyl-2-methoxycarbonyl-4-hydroxy-6,7-dimethoxynaphthalene.

Step 5

The process of Example 1, Step 5 was followed except that the mixture of 1-(3,4-dimethoxyphenyl)-2-methoxycarbonyl-4-hydroxynaphthalene and 1-phenyl-2-methoxycarbonyl-4-hydroxy-6,7-dimethoxynaphthalene (2.8 grams) from Step 4 was used and 41 mL of a 1M solution of methyl magnesium chloride in tetrahydrofuran was used. For the cyclization, 100 mL of toluene and 100 milligrams of dodecylbenzene sulfonic acid was used. An NMR spectrum showed the recovered product to have structures consistent with a mixture of 7,7-dimethyl-2,3-dimethoxy-5-hydroxy-7H-benzo[C]fluorene and 7,7-dimethyl-9,10-dimethoxy-5-hydroxy-7H-benzo[C]fluorene. This material was not purified further but was used directly in the next step as a solution in toluene.

Step 6

The process of Example 1, Step 6 was followed except that the product mixture of the preceding Step 5 and 2.1 grams of 1,1-di(4-methoxyphenyl)-2-propyn-1-ol was used. The two resulting products were separated by chromatography on silica gel using a 3:1 mixture of hexane and ethyl acetate as the elutant. Concentration of the respective fractions followed by recrystallization from ethanol (95%) yielded 336 milligrams of a first product having a melting point of 225–228° C. and 192 milligrams of a second product having a melting point of 160–162° C. NMR spectra showed the first (desired) product to have a structure consistent with the desired product, 3,3-di(4-methoxyphenyl)-6,7-dimethoxy-13,13-dimethyl-3H-13H-indeno[2,1-f]naphtho[1,2-b]pyran and the second product to have a structure consistent with 3,3-di(4-methoxyphenyl)-10,11-dimethoxy-13,13-dimethyl-3H,13H-indeno[2,1-f]naphtho[1,2-b]pyran.

EXAMPLE 5

The process of Example 3 was followed except that in Step 1 of Example 3, 6.75 grams of the product mixture from Example 4, Step 3 (1-(3,4-dimethoxyphenyl)-2-methoxycarbonyl-4-acetoxynaphthalene and 1-phenyl-2-methoxycarbonyl-4-acetoxy-6,7-dimethoxynaphthalene) was used. In Step 2 of Example 3, 500 milligrams of dodecylbenzene sulfonic acid and 150 mL of xylene (instead of toluene) were used. A mixture of indanones, 2.8 grams as a red solid, was collected by vacuum filtration. As in Step 4 of Example 3, the crude mixture of isomers from Step 3 (2.7 grams) and 6.6 mL of ethyl magnesium chloride as a 2M solution in tetrohydrofuran was used. The crude product was purified by chromatography on silica gel using a 2:1 mixture of hexane and ethyl acetate as the elutant, yielding 172 milligrams of a first product having a melting point range of 220–222° C. and 371 milligrams of a second product having a melting point of 154–157° C. An NMR spectrum showed the first (desired) product to have a structure consistent with 3,3-di(4-methoxyphenyl)-6,7-dimethoxy-13-hydroxy-13-ethyl-3H-13H-indeno[2,1-f]naphtho[1,2-b]pyran. An NMR spectra showed that the second recovered product had a structure consistent with 3,3-di(4-methoxyphenyl)-10,11-dimethoxy-13-hydroxy-13-ethyl-3H,13H-indeno[2,1-f]naphtho[1,2-b]pyran. The second product was isolated and used as Comparative Example 3 described hereinafter.

EXAMPLE 6

The process of Example 1 was followed except that in step 5 of Example 1, the reaction flask was charged with 1-(3,4-dimethoxyphenyl)-2-methoxycarbonyl-4-hydroxy-6,7-dimethoxynaphthalene (2.5 grams) under a nitrogen atmosphere and 15 mL of anhydrous tetrahydrofuran was added to the flask. The reaction mixture was cooled in an ice bath and 15 mL of ethyl magnesium chloride (2M in tetrahydrofuran) was added dropwise over 30 minutes. The resulting yellow reaction mixture was stirred at 0° C. for 1 hour, and an additional 10 ML of ethyl magnesium chloride added. The reaction mixture was slowly warmed to room temperature and stirred overnight. The reaction mixture was cooled to 0° C., an additional 10 mL of ethyl magnesium chloride added, and the reaction mixture stirred at room temperature for 24 hours. The reaction mixture was carefully poured into a beaker containing 50 mL of an ice/water mixture. Ether (20 mL) was added and the layers separated. The aqueous layer was extracted with four 50 mL portions of ether. The organic extracts were combined and washed with 40 mL of water. The organic layer was dried over anhydrous magnesium sulfate and then concentrated by rotary evaporation. The resulting yellow oil (1.9 grams) was transferred into a reaction vessel (fitted with a Dean-Stark trap) containing 30 mL of toluene to which two drops of dodecylbenzene sulfonic acid were added. The reaction mixture was heated to reflux for 2 hours, cooled, and the toluene solvent removed by rotary evaporation. The resulting dark brown solid was chromatographed on silica gel using a 1:1 hexane/ethyl acetate mixture as the elutant to provide 506 milligrams of a major product. An NMR spectrum showed the product to have a structure consistent with 7,7-diethyl-5-hydroxy-2,3,9,10-tetramethoxy-7H-benzo[C]fluorene.

Step 2

7,7-Diethyl-5-hydroxy-2,3,9,10-tetramethoxy-7H-benzo[C]-fluorene from Step 1 (200 milligrams), 4,4'-dimethoxyphenyl propargyl alcohol (250 milligrams), two drops of dodecylbenzene sulfonic acid and 20 mL of chloroform were combined in a reaction vessel and stirred at ambient temperature for 18 hours. The reaction mixture was concentrated by rotary evaporation and the residue was chromatographed on silica gel using a 1:1 mixture of hexane:ethyl acetate as the elutant. Photochromic fractions were collected, concentrated by rotary evaporation and the resulting solid recrystallized from ethanol (95%) yielding 107 mg of needles having a melting point range of 178–181° C. An NMR spectrum showed the product to have a structure consistent with 3,3-di(4-methoxyphenyl)-6,7,10,11-tetramethoxy-13,13-diethyl-3H,13H-indeno[2,1-f]naphtho[1,2-b]pyran.

EXAMPLE 7

Step 1

Sodium methoxide (6.65 grams) was weighed into a dry reaction flask under a nitrogen atmosphere. Methanol (200 mL) was added. A solution of 3,4-dimethoxybenzaldehyde (19 grams) and 3-benzoyl methyl propionate (21.5 grams) in 200 mL of methanol was added dropwise to the reaction mixture via syringe, with stirring. Stirring was continued at ambient temperature, overnight. Methanol was removed from the reaction mixture by rotary evaporation. The residual oil was dissolved in 0.5 L of water and the resulting basic solution was extracted with hexanes (200 mL). The aqueous layer was acidified with concentrated hydrochloric acid to a pH of less than 2 and extracted three times, with 200 mL portions of ethyl ether. The organic layers were combined, washed with brine (200 mL) and dried over anhydrous sodium sulfate. Removal of the solvent by rotary evaporation yielded 36.5 grams of a light yellow oil containing 3-benzoyl-4-(3,4-dimethoxyphenyl)-3-butenoic acid which was used directly in the next step.

Step 2

3-Benzoyl-4-(3,4-dimethoxyphenyl)-3-butenoic acid (15 grams) from Step 1 was placed in a reaction flask and 150 mL of acetic anhydride was added. The reaction mixture was heated and maintained at 125° C. overnight. Acetic anhydride was then removed under vacuum, and the residual dark solid was recrystallized from ethyl acetate to yield 6.6 grams of a light yellow solid. The NMR spectrum showed a single product that had a structure consistent with 1-acetoxy-3-benzoyl-6,7-dimethoxynaphthalene. The mother liquid from recrystallization was purified by column chromatography using a mixture of hexanes/ethyl acetate/methylene chloride in a volume ratio of 5/1/4 as the eluent to yield an additional 7.4 grams of the product.

Step 3

1-Acetoxy-3-benzoyl-6,7-dimethoxynaphthalene (6.6 grams) from Step 2 was added to a reaction flask containing a mixture of 100 mL of methanol and 20 mL of 37% aqueous hydrochloric acid. The reaction mixture was heated to 70° C. and stirred for 1.5 hours. Methanol was removed by rotary evaporation, and the residual mixture was dissolved in ethyl ether. The organic layer was separated. The aqueous layer was saturated with sodium chloride and extracted with ethyl acetate. The combined organic phases were washed with brine and dried over anhydrous magnesium sulfate. The solvents were removed to yield 4.75 grams of a yellow solid, 3-benzoyl-6,7-dimethoxy-1-naphthol.

Step 4

3-Benzoyl-6,7-dimethoxy-1-naphthol (2.5 grams) from Step 3 was added to a flask containing 80 mL of anhydrous tetrahydrofuran with stirring under a nitrogen atmosphere and cooled to −78° C. Phenyl lithium (14 mL of 1.8 M solution in cyclohexane/ether, 70/30) was added dropwise to the reaction mixture over a 10 minute period. The reaction mixture was left to warm to room temperature overnight. It was then quenched with water, acidified with 2N aqueous hydrochloric acid to a pH less than 3, and extracted with ethyl ether. The organic phase was washed with brine and dried over anhydrous sodium sulfate. The solvents were partially removed by rotary evaporation to give an oil which was triturated with methylene chloride to yield 2.5 grams of a light yellow solid, 6,7-dimethoxy-3-diphenylhydroxymethyl-1-naphthol.

Step 5

6,7-Dimethoxy-3-diphenylhydroxymethyl-1-naphthol (1.0 grams) from Step 4 was weighed into a reaction flask under a nitrogen atmosphere, 85% phosphoric acid (15 mL)

was added with vigorous stirring. The reaction mixture was heated to 95–100° C. After 3 hours, the reaction mixture was cooled to room temperature and poured into 250 mL of water and stirred vigorously for 10 minutes. A white solid precipitated out of the aqueous solution. The solid was filtered and washed with copious amounts of water, and dried under vacuum to get 0.9 grams of product. An NMR spectrum showed the product to have a structure consistent with 2,3-dimethoxy-5-hydroxy-7H- 7-phenyl-benzo[C]-fluorene. This material was not purified further but was used directly in the next step.

Step 6

2,3-dimethoxy-5-hydroxy-7H-7-phenyl-benzo[C]-fluorene from Step 5 (0.40 grams), 1,1-di(4-methoxyphenyl-2-propyn-1-ol (0.32 grams), dodecylbenzene sulfonic acid (about 10 milligrams), and 40 mL of toluene were combined in a reaction vessel and stirred at ambient temperature for 2 hours. The solvent was removed by rotary evaporation. The resulting brown-black solid was purified by column chromatography yielding 0.55 grams of product having a melting point of 174° C. NMR analysis showed the product to have a structure consistent with 3,3-di(4-methoxyphenyl)-6,7-dimethoxy-13-phenyl-3H,13H-indeno[2,1-f]naphtho[1,2-b] pyran.

EXAMPLE 8

The process of Step 6, Example 7 was followed except that 0.5 milligrams of 2,3-dimethoxy-5-hydroxy-7H-7-phenyl-benzo[C]-fluorene and about 20 milligrams of dodecylbenzene sulfonic acid were used. Also, 1-(4-methoxyphenyl)-1-(4-morpholinophenyl)-2-propyn-1-ol (0.44 grams) was used instead of 1,1-di(4-methoxyphenyl)-2-propyn-1-ol and methylene chloride (40 mL) was used instead of toluene. The reactants were combined in a reaction vessel and stirred at ambient temperature for 4 hours. The solvent was removed by rotary evaporation. The resulting brown-black solid was purified by column chromatography yielding 0.70 grams having a melting point of 178° C. NMR analysis showed the product to have a structure consistent with 3-(4-methoxyphenyl)-3-(4-morpholinophenyl)-6,7-dimethoxy-13-phenyl-3H, 13H-indeno[2,1-f]naphtho[1,2-b]pyran.

EXAMPLE 9

Step 1

1-Phenyl-2-methoxycarbonyl-4-hydroxy-6,7-dimethoxynaphthalene (5.0 grams) from Step 4 of Example 4 was weighed into a reaction flask under a nitrogen atmosphere and 150 mL of anhydrous tetrahydrofuran (THF) was added. Methyl magnesium chloride (25 ml of 3.0 M in THF) was added to the reaction mixture over a 15 minute period. The reaction mixture was stirred overnight and then poured into 400 mL of water. The pH of the resulting solution was adjusted to a pH of about 5 with 10 weight percent aqueous hydrochloric acid. Extraction was carried out with chloroform (three times with 200 mL). The organic layers were combined, washed with saturated aqueous NaCl solution (300 mL) and dried over anhydrous sodium sulfate. Removal of the solvent by rotary evaporation yielded 5.2 grams of a light brown solid. An NMR spectrum showed the product to have a structure consistent with 1-phenyl-2-(dimethylhydroxymethyl)-4-hydroxy-6,7-dimethoxynaphthalene. This material was not purified further but was used directly in the next step.

Step 2

The product from step 1 (1-phenyl-2-(dimethylhydroxymethyl)-4-hydroxy-6,7-dimethoxynaphthalene, (5.1 grams) was placed in a reaction flask equipped with a Dean-Stark trap and 150 mL of toluene was added. The reaction mixture was stirred under a nitrogen atmosphere and dodecylbenzene sulfonic acid (about 50 milligrams) was added. The reaction mixture was heated at reflux temperatures for 2 hours and cooled to room temperature. Removal of the solvent was done by rotary evaporation to get 5.0 grams of a dark oily solid that foamed upon drying under vacuum. An NMR spectrum showed the product to have a structure consistent with 2,3-dimethoxy-5-hydroxy-7,7-dimethyl-7[H]benzo[C]-fluorene. This material was not purified further but was used directly in the next step.

Step 3

The process of Step 6, Example 7 was followed except that 2.5 grams of 2,3-dimethoxy-5-hydroxy-7,7-dimethyl-7[H]benzo[C]-fluorene, about 40 milligrams of dodecylbenzene sulfonic acid, and 75 mL of toluene were used. Also, 1-(4-methoxyphenyl)-1-(4-morpholinophenyl)-2-propyn-1-ol (2.5 grams) was used instead of 1,1-di(4-methoxyphenyl)-2-propyn-1-ol. The reactants were combined in a reaction vessel and stirred at ambient temperature for 3 hours. The solvent was removed by rotary evaporation. The resulting brown-black solid was purified by column chromatography, and subsequently, recrystallized from methanol yielding 3.5 grams of product having a melting point of 168° C. NMR analysis showed the product to have a structure consistent with 3-(4-methoxyphenyl)-3-(4-morpholinophenyl)-6,7-dimethoxy-13,13-dimethyl-3H,13H-indeno[2,1-f]naphtho [1,2-b]pyran.

EXAMPLE 10

The process of Step 6, Example 7 was followed except that 0.8 grams of 2,3-dimethoxy-5-hydroxy-7,7-dimethyl-7[H]benzo[C]-fluorene, about 20 milligrams of dodecylbenzene sulfonic acid and 75 mL each of chloroform and toluene were used. Also, 1-(4-methoxyphenyl)-1-(4-dimethylaminophenyl)-2-propyn-1-ol (0.7 grams) was used instead of 1,1-di(4-methoxyphenyl)-2-propyn-1-ol. The reactants were combined in a reaction vessel and stirred at ambient temperature for two and a half hours. The solvent was removed by rotary evaporation. The resulting brown-black solid was purified by recrystallization from methanol yielding 1.1 grams of product having a melting point of 198° C. NMR analysis showed the product to have a structure consistent with 3-(4-methoxyphenyl)-3-(4-dimethylaminophenyl)-6,7-dimethoxy-13,13-dimethyl-3H, 13H-indeno[2,1-f]naphtho[1,2-b]pyran.

EXAMPLE 11

Step 1

Sodium methoxide (15.2 grams) was weighed into a dry reaction flask. Methanol (100 mL) was added and a nitrogen atmosphere was established. A mixture of 2,3,4-trimethoxybenzaldehyde (50 grams) and 3-benzoyl methyl propionate (50 grams) in 150 mL of methanol was added to the reaction mixture with stirring over a 90 minute period. After stirring an additional 2 hours, the reaction mixture was poured into 600 mL of water. The reaction mixture was extracted with 250 mL of ether four times. The pH of the aqueous layer was adjusted to about 5 with concentrated hydrochloric acid. A yellowish oil was obtained. It was extracted three times with 200 mL portions of methylene chloride. The organic layers were combined, washed with saturated aqueous NaCl solution (300 mL) and dried over anhydrous sodium sulfate. Removal of the solvent by rotary evaporation yielded 90 grams of a light yellow oil. A nuclear magnetic resonance (NMR) spectrum showed the product to have a structure consistent with 3-benzoyl-4-(2,3,4-trimethoxyphenyl)-3-butenoic acid. This material was not purified further but was used directly in the next step.

Step 2

3-Benzoyl-4-(2,3,4-trimethoxyphenyl)-3-butenoic acid (47 grams) from Step 1 was placed in a reaction flask and 200 mL of acetic anhydride and 8.4 grams of sodium acetate were added. The reaction mixture was heated to reflux temperatures for 2 hours and cooled to room temperature. The solvent (acetic anhydride) was removed by rotary evaporation. The resulting residue was dissolved in 400 mL of methylene chloride and 400 mL of water was added. Solid sodium carbonate was added to the biphasic mixture until bubbling ceased. The layers separated and the aqueous layer was extracted with two 100 mL portions of methylene chloride. The organic layers were combined, washed with saturated NaCl solution (300 mL) and dried over anhydrous sodium sulfate. The solvent (methylene chloride) was removed by rotary evaporation to yield a red oil. An NMR spectrum showed the product to have a structure consistent with 2-benzoyl-4-acetoxy-6,7,8-trimethoxynaphthalene. This material was not purified further but was used directly in the next step.

Step 3

2-Benzoyl-4-acetoxy-6,7,8-trimethoxynaphthalene (45 grams) from Step 2 and 250 mL of methanol were combined in a reaction flask. A mixture of 100 grams of 50 weight percent aqueous NaOH solution and 200 mL of water were added to the reaction flask and the resulting mixture was heated to reflux for 2 hours. The reaction mixture was cooled and then poured into 500 mL of water. The pH of the aqueous layer was adjusted to a pH of about 5 with concentrated hydrochloric acid. Extraction was done with three 300 mL portions of chloroform. The organic layers were combined, washed with saturated NaCl solution (300 mL) and dried over anhydrous sodium sulfate. The solvent (chloroform) was removed by rotary evaporation to yield a brownish-red oily solid. An NMR spectrum showed the product to have a structure consistent with 2-benzoyl-4-hydroxy-6,7,8-trimethoxynaphthalene. This material was not purified further but was used directly in the next step.

Step 4

2-Benzoyl-4-hydroxy-6,7,8-trimethoxynaphthalene (9.9 grams) from Step 3 was added to a reaction flask containing 100 mL of anhydrous tetrahydrofuran and stirred under a nitrogen atmosphere at room temperature. Phenyl lithium (50 mL of a 1.8 M ether solution) was added dropwise to the reaction mixture with stirring over a 30 minute period. After stirring for an additional 2 hours at ambient temperature, the reaction mixture was poured into 500 mL of water. The pH of the aqueous layer was adjusted to a pH of about 5 with concentrated hydrochloric acid. Extraction was done with three 200 mL portions of ethyl acetate. The organic layers were combined, washed with saturated NaCl solution (300 mL) and dried over anhydrous sodium sulfate. The solvent (ethyl acetate) was removed by rotary evaporation to yield 12.0 grams of a brownish oil. An NMR spectrum showed the product to have a structure consistent with 2-(diphenylhydroxymethyl)-4-hydroxy-6,7,8-trimethoxy-naphthalene. This material was not purified further but was used directly in the next step.

Step 5

2-(Diphenylhydroxymethyl)-4-hydroxy-6,7,8-trimethoxy-naphthalene (10.0 grams) from Step 4 was weighed into a reaction flask under a nitrogen atmosphere and 80 mL of 85% phosphoric acid was added accompanied by vigorous stirring. The reaction mixture was heated to 110–120° C. After 2 hours, the reaction mixture was cooled to room temperature and poured into 250 mL of water and stirred vigorously for 10 minutes. A gray oily solid precipitated out of the aqueous solution. Extraction was done with three 200 mL portions of chloroform. The organic layers were combined, washed with a saturated aqueous sodium bicarbonate solution (300 mL), saturated NaCl solution (300 mL), and dried over anhydrous sodium sulfate. The solvent (chloroform) was removed by rotary evaporation to yield a gray oily solid. A nuclear magnetic resonance (NMR) spectrum showed the product to have a structure consistent with 1,2,3-trimethoxy-5-hydroxy-7H-7-phenyl-benzo[C]-fluorene. This material was not purified further but was used directly in the next step.

Step 6

1,2,3-Trimethoxy-5-hydroxy-7,7-dimethyl-7[H]benzo[C]-fluorene (1.75 grams) from Step 5, 1.2 grams of 1,1-di(4-methoxyphenyl-2-propyn-1-ol, dodecylbenzene sulfonic acid (about 20 milligrams), and 125 mL of methylene chloride were combined in a reaction vessel and stirred at ambient temperature overnight. The solvent was removed by rotary evaporation. The resulting dark solid was purified by column chromatography, and subsequently, recrystallized from methanol yielding 0.84 gram of product having a melting point of 192° C. NMR analysis showed the product to have a structure consistent with 3,3-di(4-methoxyphenyl)-6,7,8-trimethoxy-13-phenyl-3H,13H-indeno[2,1-f]naphtho[1,2-b]pyran.

EXAMPLE 12

The process of Example 3 was followed except for the following: in Step 3, 3,3-di-(4-methoxyphenyl)-6,7,10,11-tetramethoxy-13-oxo-3H,13H-indeno[2,1-f]naphtho[1,2-b]pyran (1 gram), 3-(4-methoxy)-3-(4-morpholino)-2-propyn-1-ol (1.3 grams) and 80 mL of chloroform were used; in Step 4, 3-(4-methoxy)-3-(4-morpholino)-6,7,10,11-tetramethoxy-13-oxo-3H,13H-indeno[2,1-f]naphtho[1,2-b]pyran (1 gram), and ethyl magnesium chloride (10 mL of a 2M solution), and 25 mL of THF were used. The resulting product was chromatographed on silica gel using 2:1 hexanes/ethyl acetate eluent followed by recrystallization from methanol to provide 608 mg of a product having a melting point of 182–184° C. An NMR spectrum showed the product to have a structure consistent with 3-(4-methoxyphenyl)-3-(4-morpholinophenyl)-6,7,10,11-tetramethoxy-13-hydroxy-13-ethyl-3H,13H-indeno[2,1-f]naphtho[1,2-b]pyran.

EXAMPLE 13

The process of Example 3 was used except for the following: in Step 3, 3,3-di-(4-methoxyphenyl)-6,7,10,11- tetramethoxy-13-oxo-3H,13H-indeno[2,1-f]naphtho[1,-b] pyran (6.43 grams), 3-(4-methoxy)-3-(4-morpholino)-2-propyn-1-ol (3.9 grams) and 200 mL of chloroform were used; in Step 4, 3-(4-methoxy)-3-(4-morpholino)-6,7,10,11-tetramethoxy-13-oxo-3H,13H-indeno[2,1-f]naphtho[1,2-b] pyran (3 grams), butyllithium (5.2 mL of a 1.4 M solution in THF), and 100 mL of THF were used. The resulting product was chromatographed on silica gel using 1:1 hexanes/ethylacetate eluent followed by recrystallization from acetonitrile to provide 708 mg of a product having a melting point of 251–252° C. An NMR spectrum showed the product to have a structure consistent with 3-(4-methoxyphenyl)-3-(4-morpholinophenyl)-6,7,10,11-tetramethoxy-13-hydroxy-13-butyl-3H,13H-indeno[2,1-f]naphtho[1,2-b]pyran.

EXAMPLE 14

Step 1

The process of Step 1, Example 4 was followed except that 292 grams of 1,2-dimethoxy benzene, 297 grams of benzoyl chloride, and 281 grams of aluminum chloride were used to yield 490 grams of 3,4-dimethoxy benzophenone.

Step 2

The process of Step 2, Example 4 was followed except that 490 grams of 3,4-dimethoxybenzophenone and 354 grams of dimethyl succinate were dissolved in toluene (2500 mL) at ~45° C., and 248 grams of potassium-t-butoxide was added portionwise maintaining the temperature at ~45° C. After stirring for 12 hours, the mixture was poured into 5000 mL of water and vigorously agitated for 20 minutes. The aqueous and organic phases were separated and the organic phase was extracted with 500 mL portions of water two times. The combined aqueous fractions were acidified to pH 2 with 6N hydrochloric acid and 1000 mL of toluene was added. The mixture was agitated, and the toluene layer separated. The toluene extract was concentrated by rotary evaporation to yield 500 grams of an oil. An NMR spectrum showed the product to have structures consistent with a mixture of (E and Z) 4-(3,4-dimethoxyphenyl)-4-phenyl-3-methoxycarbonyl-3-butenoic acids, but strongly enriched in the E isomer.

Step 3

The oil isolated from Step 2 was heated to reflux in 2.1 L of acetic anhydride under a nitrogen atmosphere. The reaction mixture was cooled and the acetic anhydride was removed by rotary evaporation to yield a thick gum, which solidified upon standing. The solid was dissolved in boiling methanol (3 L) and allowed to cool overnight. The crystals that formed were collected by vacuum filtration, washed with methanol and then air-dried. An NMR spectrum showed the crystals (249 grams) to have a structure consistent with 1-phenyl-2-methoxycarbonyl-4-acetoxy-6,7-dimethoxynaphthalene. The isomer 1-(3,4-dimethoxyphenyl)-2-methoxycarbonyl-4-acetoxynaphthalene remained in the filtrate as a mixture with 1-phenyl-2-methoxycarbonyl-4-acetoxy-6,7-dimethoxynaphthalene.

Step 4

1-Phenyl-2-methoxycarbonyl-4-acetoxy-6,7-dimethoxynaphthalene (66.4 grams) from Step 3, 500 mL of a 10 weight percent aqueous sodium hydroxide solution and 50 mL of methanol were added to a reaction flask and heated to reflux for 3 hours and then cooled to room temperature. The reaction mixture was poured onto an aqueous solution of 4N hydrochloric acid/ice mixture (~400 mL). A white precipitate formed and was collected by vacuum filtration, washed with water and was air-dried. Recrystallization from ethanol (95 weight percent) gave 57 grams of 1-phenyl-4-hydroxy-6,7-dimethoxy-2-naphthoic acid.

Step 5

1-Phenyl-4-hydroxy-6,7-dimethoxy-2-naphthoic acid, (55 grams) from Step 4, and dodecylbenzenesulfonic acid (1 gram) were added to a reaction flask containing 1 liter of xylene and heated to reflux for 36 hours. The reaction was cooled and the resulting red precipitate was collected by vacuum filtration and washed with toluene. The red solid was air-dried yielding 48.1 grams of product. An NMR spectrum showed the product to have a structure consistent with 2,3-dimethoxy-5-hydroxy-7H-benzo[C]fluoren-7-one.

Step 6

The process of Example 3, Step 3 was followed except 2,3-dimethoxy-5-hydroxy-7H-benzo[C]fluoren-7-one (13.5 grams) from Step 5 above was used instead of 2,3,9,10-tetramethoxy-5-hydroxy-7H-benzo[C]fluoren-7-one and 8 grams of 1-(4-morpholinophenyl)-1-phenyl-2-propyn-1-ol was used in place of 1,1-di(4-methoxyphenyl)-2-propyn-1-ol, and 250 mL of chloroform were used. Red needles (5 grams) having an NMR spectrum consistent with 3-(4-morpholinophenyl)-3-phenyl-6,7-dimethoxy-13-oxo-3H, 13H-indeno[2,1-f]naphtho[1,2-b]pyran were isolated by filtration from a few mL of cold acetone.

Step 7

3-(4-morpholinophenyl)-3-phenyl-6,7-dimethoxy-13-oxo-3H,13H-indeno[2,1-f]naphtho[1,2-b]pyran (5 grams) from Step 6 was added to a reaction flask containing THF (100 mL). Under a nitrogen atmosphere at 0° C., an excess of ethyl magnesium chloride (20 mL of a 2 M solution in THF) was added to the reaction flask. The resulting reaction was stirred at 0° C. for 30 minutes and then warmed to room temperature. The reaction mixture was poured onto 200 mL of ice water then acidified to pH 3 with an aqueous 2N hydrochloric acid solution. Diethylether (100 mL) was added and the organic phase separated. The solvents were removed by rotary evaporation and the resulting oil was chromatographed on a silica column using hexane:ethyl acetate (2:1) as eluant. The photochromic fractions were concentrated and the residue crystallized from methanol to give 2 grams of a white solid (m.p. 208–209° C.) An NMR spectrum showed the product to have a structure consistent with 3-(4-morpholinophenyl)-3-phenyl-6,7-dimethoxy-13-hydroxy-13-ethyl-3H,13H-indeno[2,1,-f]naphtho[1,2-b] pyran.

EXAMPLE 15

The procedure for Example 14 was followed except that in Step 6 1-di(4-methoxyphenyl)-2-propyn-1-ol was used in place of 1-(4-morpholino-phenyl)-1-phenyl-2-propyn-1-ol. The resulting purple crystals (14.5 grams) had an NMR spectrum showing the product to have a structure consistent with 3,3-di(4-methoxyphenyl)-6,7-dimethoxy-13-oxo-3H, 13H-indeno[2,1-f]naphtho[1,2-b]pyran. In Step 7, 1.8 grams of 3,3-di( 4-methoxyphenyl)-6,7-dimethoxy-13-oxo-3H, 13H-indeno[2,1-f]naphtho[1,2-b]pyran in 30 mL of THF was used and n-butyllithium (2.5 mL of a 2.5 M solution in THF) was used instead of ethyl magnesium chloride. The resulting oil was chromatographed on silica gel using 3:1 hexanes/ethyl acetate as eluent. Recrystallization from 3:1 hexanes/ethyl acetate provided 518 mg of a beige solid having a melting point of 193–195° C. An NMR spectrum showed the product to have a structure consistent with 3,3-di(4-methoxyphenyl)-6,7-dimethoxy-13-hydroxy-13-butyl-3H,13H-indeno[2,1,-f]naphtho[1,2-b]pyran.

EXAMPLE 16

The procedure for Example 14 was followed except in Step 7, 3-(4-morpholino)-3-phenyl-(6,7-dimethoxy-13-oxo-3H,13H-indeno[2,1-f]naphtho[1,2-b]pyran (1.0 gram) and n-butyllithium (1.36 mL of a 2.5 M solution in THF) was used in place of ethyl magnesium chloride. The resulting oil was chromatographed on silica gel using 2:1 hexanes/ethyl acetate as the eluent. Recrystallization from methylene chloride/ethanol (95%) provided a beige powder (310 mg) which had a melting point of 230–231° C. An NMR spectrum showed the product to have a structure consistent with 3-(4-morpholinophenyl)-3-phenyl-6,7-dimethoxy-13-hydroxy-13-butyl-3H,13H-indeno[2,1,-f]naphtho[1,2-b]pyran.

EXAMPLE 17

Step 1

2,3-Dimethoxy-5-hydroxy-7H-benzo[C]-fluoren-7-one (3.0 grams, 9.8 mmol) from Step 5, Example 14 was added to a reaction flask containing 400 mL of chloroform. A catalytic amount of p-dodecylbenzene sulfonic acid (about 50 mg) was added to a reaction flask followed by the addition of 1-(4-methoxyphenyl)-1-(4-morpholinophenyl)-2-propyn-1-ol (1.3 grams). The reaction mixture was stirred at ambient temperature overnight. An additional portion of 1-(4-methoxyphenyl)-1-(4-morpholinophenyl)-2-propyn-1-ol (0.97 grams) was added and the stirring was continued for 8 hours. The unreacted 6,7-dimethoxy-5-hydroxy-7H-benzo[C]-fluoren-7-one (2.1 grams, 6.7 mmol) was removed by filtration. The filtrate was stripped off the solvent and triturated with acetone to yield 1.88 grams of a red solid that displayed photochromism in solution. The product, 6,7-dimethoxy-3-(4-methoxyphenyl)-3-(4-morpholinophenyl)-13-oxo-3H,13H-indeno[2,1-f]naphtho[1,2-b]pyran, was taken on to the next step without further purification.

Step 2

6,7-Dimethoxy-3-(4-methoxyphenyl)-3-(4-morpholinophenyl)-13-oxo-3H,13H-indeno[2,1-f]naphtho[1,2-b]pyran from Step 1 (1.88 grams) was added to a dry reaction flask under a nitrogen atmosphere. Anhydrous tetrahydrofuran (75 mL) was added and the reaction mixture was stirred to form a red suspension. Ethyl magnesium chloride (4 mL of a 2 M solution in tetrahydrofuran) was added dropwise, with stirring, at ambient temperature. Upon completion of ethyl magnesium chloride addition, the red suspension became a brown solution. The reaction mixture was stirred for an additional 40 minutes and quenched with water (100 mL). The organic phase was separated, the aqueous phase was neutralized with 2N hydrochloric acid to a pH of 7. The aqueous phase was extracted three times with 50 mL portions of ethyl ether. All of the organic phases were combined and dried over anhydrous sodium sulfate. The solvents were removed by rotary evaporation. The resulting oily substance was recrystallized from ethyl acetate to yield 0.93 g of a light solid having a melting point of 156–157° C. The NMR spectra showed the product to have a structure consistent with 6,7-dimethoxy-3-(4-methoxyphenyl)-3-(4-morpholinophenyl)-13-hydroxy-13-ethyl-3H,13H-indeno[2,1-f]naphtho[1,2-b]pyran.

EXAMPLE 18

6,7-Dimethoxy-3-(4-methoxyphenyl)-3-(4-morpholinophenyl)-13-hydroxy-13-ethyl-3H,13H-indeno[2,1-f]naphtho[1,2-b]pyran (0.6 gram) from Step 2 of Example 17 was added to a reaction flask containing 50 mL of methanol. Concentrated (37%) hydrochloric acid (10 mL) was slowly added to the suspension and formation of a solution was observed. The solution was left to stir overnight at ambient temperature. Potassium hydroxide in methanol was added until a neutral pH was obtained. The solvent was removed under vacuum. The resulting solid was separated by filtration. The aqueous filtrate was extracted with ethyl acetate. The ethyl acetate was removed under vacuum and the organic solids were combined and purified by column chromatography using a mixture of acetone/hexanes in a volume ratio of 40/60 as the eluent. The collected photochromic fractions were further purified by recrystallization from methanol to yield 0.11 grams of a white solid having a melting point of 175–176° C. The NMR spectra showed the product to have a structure consistent with 3-(4-methoxyphenyl)-3-(4-morpholinophenyl)-6,7-dimethoxy-13-ethyl-13-methoxy-3H,13H-indeno[2,1-f]naphtho[1,2-b]pyran.

EXAMPLE 19

6,7-Dimethoxy-3-(4-methoxyphenyl)-3-(4-morpholinophenyl)-13-oxo-3H,13H-indeno[2,1-f]naphtho[1,2-b]pyran (1.55 grams) from Step 1 of Example 17 was added to a dry reaction flask under a nitrogen atmosphere. Anhydrous tetrahydrofuran (250 mL) was added and the reaction mixture was stirred to form a red suspension. Methyl lithium (2.3 mL of a 1.4 M solution in ethyl ether) was added dropwise, with stirring, at ambient temperature. Upon completion of the methyl lithium addition, the red suspension became a brown colored solution. The reaction mixture was stirred an additional 40 minutes and quenched with water (100 mL) and then the pH was adjusted with 2N hydrochloric acid to a pH of 6. The reaction mixture was extracted three times with 100 mL portions of ethyl ether, the organic phases were combined and dried over anhydrous sodium sulfate. The solvents were removed by rotary evaporation. The residue was recrystallized from methanol to yield 0.95 g of light solid with the melting point of 199–200° C. The product decomposed at this temperature. The NMR spectra showed the product to have a structure consistent with 3-(4-methoxyphenyl)-3-(4-morpholinophenyl)-6,7-dimethoxy-13-hydroxy-13-methyl-3H,13H-indeno[2,1-f]naphtho[1,2-b]pyran.

EXAMPLE 20

The process of Example 18 was followed except that 6,7-dimethoxy-3-(4-methoxyphenyl)-3-(4-morpholinophenyl)-13-hydroxy-13-methyl-3H,13H-indeno[2,1-f]naphtho[1,2-b]pyran (0.2 grams) was used instead of 3-(4-methoxyphenyl)-3-(4-morpholinophenyl)-6,7-dimethoxy-13-hydroxy-13-ethyl-3H,13H-indeno[2,1-f]naphtho[1,2-b]pyran, boiling methanol was added instead of methanol at room temperature, 0.6 mL of concentrated hydrochloric acid was used instead of 10 mL, and stirring at ambient temperature continued for 2 days, as opposed to overnight. The resulting light solid (70 milligrams) had a melting point of 176–177° C. The NMR spectra showed the product to have a structure consistent with 3-(4-methoxyphenyl)-3-(4-morpholinophenyl)-6,7-dimethoxy-13-methoxy-13-methyl-3H,13H-indeno[2,1-f]naphtho[1,2-b]pyran.

COMPARATIVE EXAMPLES 1–3

Three indeno[2,1-f]naphtho[1,2-b]pyrans lacking a substituent on at least two of the 5-, 6-, 7- and 8-positions were prepared following similar processes to those of Examples 1–6. The compounds of the Comparative Examples were determined to be:

(1) 3,3-di(4-methoxyphenyl)-13-hydroxy-13-ethyl-3H-13H-indeno[2,1-f]naphtho[1,2-b]pyran;

(2) 3,3-di(4-methoxyphenyl)-6,11-dimethoxy-13-hydroxy-13-ethyl-3H-13H-indeno[2,1-f]naphtho[1,2-b]pyran; and (3) 3,3-di(4-methoxyphenyl)-10,11-dimethoxy-13-hydroxy-13-ethyl-3H-13H-indeno[2,1-f]naphtho[1,2-b]pyran.

EXAMPLE 21

Part A

Testing was done with the photochromic compounds described in Examples 1 through 20 and Comparative Examples 1 through 3 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares of Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm2). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta$OD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where % Ta is the percent transmittance in the activated state and the logarithm is to the base 10.

The optical properties of the photochromic compounds in the test squares are reported in Table 1. The $\Delta$OD/Min, which represents the sensitivity of the photochromic compound's response to UV light, was measured over the first five (5) seconds of UV exposure, then expressed on a per minute basis. The saturation optical density ($\Delta$OD@ Saturation) was taken under identical conditions as the $\Delta$OD/Min, except UV exposure was continued for 15 minutes.

The lambda max (Vis) is the wavelength in the visible spectrum at which the maximum absorption of the activated (colored) form of the photochromic compound in a test square occurs. The lambda max (Vis) wavelengths reported in Table 1 were determined by testing the photochromic test square polymerizates of Part A in a Varian Cary 3 uv-visible spectrophotometer. The bleach rate (T 1/2) is the time interval in seconds for the absorbance of the activated form of the photochromic compound in the test squares to read one half the highest absorbance at room temperature (72° F., 22.2° C.) after removal of the source of activating light.

Each of the compounds of the Examples and the Comparative Examples exhibited dual peak absorptions in the visible spectrum (lambda max visible) in distinct color regions. For each lambda max visible, the corresponding optical density ($\Delta$ OD/Min and $\Delta$ OD at saturation) for the desired compounds of the Examples and Comparative Examples are tabulated in Table 1 for the two bands (A and B) of peak absorption for each compound. Table 1 also includes the bleach rate (T 1/2) for each of the compounds as measured at band B. The ratings of the Relative $\Delta$ OD at Saturation Test for the bands A and B of each of the Examples and Comparative Examples are calculated as follows: $\Delta$ OD at saturation (Band A)/$\Delta$ OD at saturation (Band B)×100. The ratings of the Relative $\Delta$ OD at Saturation Test for each of the compounds is tabulated in Table 2.

TABLE 1

| Compound Example | Sensitivity ΔOD/MIN | ΔOD @ Saturation | Bleach Rate T ½ sec | λ MAX (nm) Vis |
|---|---|---|---|---|
| 1 (Band A) | 0.33 | 0.99 | | 445 |
| 1 (Band B) | 0.24 | 0.79 | 526 | 611 |
| 2 (Band A) | 0.32 | 1.10 | | 485 |
| 2 (Band B) | 0.29 | 1.07 | 854 | 618 |
| 3 (Band A) | 0.34 | 0.62 | | 460 |
| 3 (Band B) | 0.24 | 0.41 | 155 | 623 |
| 4 (Band A) | 0.39 | 1.11 | | 455 |
| 4 (Band B) | 0.22 | 0.71 | 267 | 576 |
| 5 (Band A) | 0.26 | 0.42 | | 458 |
| 5 (Band B) | 0.19 | 0.27 | 87 | 584 |
| 6 (Band A) | 0.46 | 1.02 | | 440 |
| 6 (Band B) | 0.37 | 0.73 | 310 | 608 |
| 7 (Band A) | 0.17 | 0.66 | | 460 |
| 7 (Band B) | 0.16 | 0.43 | 206 | 577 |
| 8 (Band A) | 0.14 | 0.43 | | 484 |
| 8 (Band B) | 0.18 | 0.44 | 179 | 603 |
| 9 (Band A) | 0.18 | 0.60 | | 477 |
| 9 (Band B) | 0.23 | 0.59 | 204 | 597 |
| 10 (Band A) | 0.20 | 0.41 | | 500 |
| 10 (Band B) | 0.28 | 0.50 | 130 | 615 |
| 11 (Band A) | 0.28 | 0.66 | | 482 |
| 11 (Band B) | 0.25 | 0.62 | 183 | 581 |
| 12 (Band A) | 0.26 | 0.46 | | 480 |
| 12 (Band B) | 0.27 | 0.43 | 130 | 632 |
| 13 (Band A) | 0.27 | 0.39 | | 482 |
| 13 (Band B) | 0.25 | 0.37 | 85 | 634 |
| 14 (Band A) | 0.24 | 0.41 | | 485 |
| 14 (Band B) | 0.22 | 0.40 | 108 | 600 |
| 15 (Band A) | 0.29 | 0.37 | | 457 |
| 15 (Band B) | 0.18 | 0.22 | 76 | 579 |
| 16 (Band A) | 0.22 | 0.37 | | 485 |
| 16 (Band B) | 0.19 | 0.35 | 113 | 600 |
| 17 (Band A) | 0.21 | 0.25 | | 480 |
| 17 (Band B) | 0.18 | 0.24 | 84 | 603 |
| 18 (Band A) | 0.21 | 0.27 | | 483 |
| 18 (Band B) | 0.18 | 0.27 | 86 | 604 |
| 19 (Band A) | 0.18 | 0.34 | | 481 |
| 19 (Band B) | 0.22 | 0.35 | 98 | 603 |
| 20 (Band A) | 0.16 | 0.34 | | 483 |
| 20 (Band B) | 0.17 | 0.37 | 105 | 604 |
| Comp. Ex. 1 (B and A) | 0.21 | 0.16 | | 437 |
| Comp. Ex. 1 (B and B) | 0.29 | 0.27 | 47 | 562 |
| Comp. Ex. 2 (B and A) | 0.22 | 0.36 | | 499 |
| Comp. Ex. 2 (B and B) | 0.32 | 0.51 | 130 | 607 |
| Comp. Ex. 3 (B and A) | 0.32 | 0.34 | | 445 |
| Comp. Ex. 3 (B and B) | 0.48 | 0.48 | 76 | 600 |

TABLE 2

| Compound Example | Relative ΔOD at Saturation |
|---|---|
| 1 | 125 |
| 2 | 103 |
| 3 | 151 |
| 4 | 156 |
| 5 | 155 |
| 6 | 140 |
| 7 | 153 |
| 8 | 98 |
| 9 | 102 |
| 10 | 82 |
| 11 | 106 |
| 12 | 106 |
| 13 | 105 |
| 14 | 103 |
| 15 | 168 |
| 16 | 106 |
| 17 | 104 |
| 18 | 100 |
| 19 | 97 |
| 20 | 92 |
| Comp. Ex. 1 | 59 |
| Comp. Ex. 2 | 70 |
| Comp. Ex. 3 | 71 |

The data presented in Tables 1 and 2 show that each tested compound of the present invention has two absorption peaks in the visible spectrum and a rating greater than 80 in the Relative ΔOD at Saturation Test.

This data demonstrates that a single compound of the present invention exhibits a blended activated hue. In the preparation of photochromic articles with a desired activated hue, a combination of complementary photochromic compounds each having an activated visible absorption maximum may be used. The activated visible absorption maxima of the various compounds are thereby blended to achieve the desired activated color. By employing a compound of the present invention having two activated visible absorption maxima, fewer distinct compounds are required to achieve a blend of activated visible absorption maxima to produce the desired activated hue, e.g. neutral color. In addition, the blended activated hue of a compound of the present invention is particularly suitable for use in photochromic articles having a brown activated hue due to the greater optical density of band A (420–500 nm) than the optical density of band B (500–650 nm).

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound of indeno[2,1-f]naphtho[1,2-b]pyran structure, represented by the following graphic formula I:

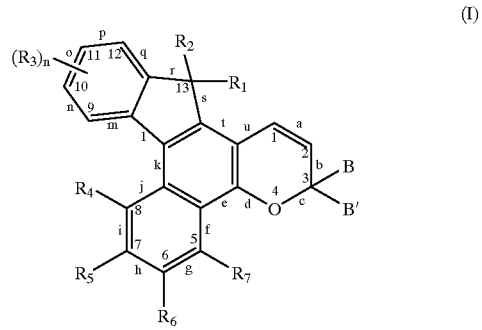

wherein, (a) in the 7 position, a group $R_5$ selected from the group consisting of:

(i) the group, $-OR_8'$, wherein $R_8'$ is phenyl($C_1-C_3$) alkyl, $C_1-C_6$ alkyl, mono($C_1-C_6$)alkyl substituted phenyl($C_1-C_3$)alkyl, mono($C_1-C_6$)alkoxy substituted phenyl($C_1-C_3$)alkyl, $C_1-C_6$ alkoxy($C_2-C_4$) alkyl, $C_3-C_7$ cycloalkyl, mono($C_1-C_4$)alkyl substituted $C_3-C_7$ cycloalkyl, $C_1-C_6$ chloroalkyl, $C_1-C_6$ fluoroalkyl, allyl, or $R_8'$ is the group, —CH($R_9$)Q, wherein $R_9$ is hydrogen or $C_1$–$C_3$ alkyl; and
(ii) a group selected from:
(1) —N($R_{15}$)$R_{16}$ wherein $R_{15}$ and $R_{16}$ are each selected from the group consisting of hydrogen, $C_1$–$C_8$ alkyl, phenyl, naphthyl, the heteroaromatic groups, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl and $C_1$–$C_{20}$ alkoxyalkyl, wherein said aryl group is phenyl or naphthyl;
(2) a nitrogen containing ring represented by the following graphic formula:

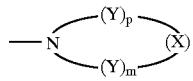

wherein Y is selected from the group consisting of —CH$_2$—, —CH($R_{17}$)—, —C($R_{17}$)($R_{17}$)—, —CH(aryl)—, —C(aryl)$_2$—, and —C($R_{17}$)(aryl)—, and X is selected from the group consisting of —Y—, —O—, —S—, —(O)—, —S(O$_2$)—, —NH—, —NR$_{17}$— and —N-aryl, wherein $R_{17}$ is $C_1$–$C_6$ alkyl, said aryl substituent is phenyl or naphthyl, m is the integer 1, 2 or 3, and p is the integer 0, 1, 2, or 3 and when p is O, X is Y; and
(3) a group represented by the following graphic formulae:

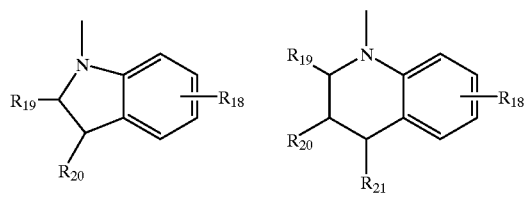

wherein $R_{19}$, $R_{20}$ and $R_{21}$ are each hydrogen, $C_1$–$C_5$ alkyl, phenyl or naphthyl, or the groups $R_{19}$ and $R_{20}$ together form a ring of 5 to 8 carbon atoms and $R_{18}$ is $C_1$–$C_6$ alkyl, $C_{1-6}$ alkoxy, fluoro or chloro;
(b) in the 6 position, a group $R_6$, said group being the same as $R_5$, defined hereinbefore; or
(c) $R_5$ and $R_6$ together form the following graphic formula:

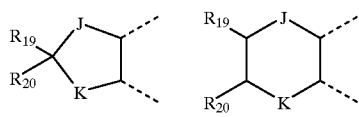

wherein J and K are each oxygen or the group —NR$_{15}$—;
(d) optionally, in the 8 position, a group $R_4$, said group being the same as $R_5$ defined hereinbefore; and
(e) in the 3 position, weak to moderate electron donor substituents, and optional substituents at the 5-, 8-, 9-, 10-, 11-, 12- or 13-positions provided that said naphthopyran demonstrates a rating of at least 80 in the Relative ΔOD at Saturation Test.

2. The naphthopyran compound of claim 1 wherein,
(a) $R_1$ and $R_2$ are each selected from the group consisting of:
(i) hydrogen, hydroxy, $C_1$–$C_6$ alkyl, amino, mono- or di-substituted amino, $C_3$–$C_7$ cycloalkyl, allyl, benzyl, mono-substituted benzyl, chloro, fluoro, the group, —C(O)W, wherein W is hydroxy, $C_1$–$C_6$ alkyl, $C_1$–$C_6$ alkoxy, phenyl, mono-substituted phenyl, amino, mono($C_1$–$C_6$)alkylamino, di($C_1$–$C_6$) alkylamino, morpholino, piperidino or pyrrolidyl, said amino substituents being selected from the group consisting of $C_1$–$C_6$ alkyl, phenyl, benzyl and naphthyl, said benzyl and phenyl substituents being $C_1$–$C_6$ alkyl or $C_1$–$C_6$ alkoxy;
(ii) the unsubstituted, mono- di- or trisubstituted groups phenyl, naphthyl, phenanthryl, pyrenyl, quinolyl, isoquinolyl, benzofuranyl, thienyl, benzothienyl, dibenzofuranyl, dibenzothienyl, carbazolyl, indolyl, said group substituents in (a)(ii) being selected from the group consisting of chloro, fluoro, $C_1$–$C_6$ alkyl and $C_1$–$C_6$ alkoxy;
(iii) monosubstituted phenyl, having a substituent at the para position that is a linking group, —(CH$_2$)$_t$— or —O—(CH$_2$)$_t$—, wherein t is the integer 1, 2, 3, 4, 5 or 6, connected to an aryl group, which is a member of another photochromic naphthopyran;
(iv) the group, —OR$_8$ wherein $R_8$ is $C_1$–$C_6$ alkyl, $C_1$–$C_6$ acyl, phenyl($C_1$–$C_3$)alkyl, mono($C_1$–$C_6$)alkyl substituted phenyl($C_1$–$C_3$)alkyl, mono($C_1$–$C_6$) alkoxy substituted phenyl($C_1$–$C_3$)alkyl, $C_1$–$C_6$ alkoxy($C_2$–$C_4$)alkyl, $C_3$–$C_7$ cycloalkyl, mono ($C_1$–$C_4$)alkyl substituted $C_3$–$C_7$ cycloalkyl, $C_1$–$C_6$ chloroalkyl, $C_1$–$C_6$ fluoroalkyl, allyl, benzoyl, monosubstituted benzoyl, naphthoyl or monosubstituted naphthoyl, said benzoyl and naphthoyl group substituents being $C_1$–$C_6$ alkyl or $C_1$–$C_6$ alkoxy, or $R_8$ is the group —CH($R_9$)Q, wherein $R_9$ is hydrogen or $C_1$–$C_3$ alkyl and Q is —CN, —CF$_3$, or —COOR$_{10}$, and $R_{10}$ is hydrogen or $C_1$–$C_3$ alkyl, or $R_8$ is the group, —C(O)V, wherein V is hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, the unsubstituted, mono- or di-substituted aryl groups, phenyl and naphthyl, amino, mono($C_1$–$C_6$)alkylamino, di($C_1$–$C_6$) alkylamino, phenylamino, mono- or di-($C_1$–$C_6$)alkyl substituted phenylamino, or mono- or di-($C_1$–$C_6$)alkoxy substituted phenylamino, said aryl group substituents being $C_1$–$C_6$ alkyl or $C_1$–$C_6$ alkoxy;
(v) the group —CH(Q')$_2$ wherein Q' is —CN or —COOR$_{11}$, wherein $R_{11}$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, or the unsubstituted, mono- or di-substituted aryl groups phenyl or naphthyl, each of said phenyl and naphthyl group substituents being $C_1$–$C_6$ alkyl or $C_1$–$C_6$ alkoxy;
(vi) the group —CH($R_{12}$)G, wherein $R_{12}$ is hydrogen, $C_1$–$C_6$ alkyl or the unsubstituted, mono- or di-substituted aryl groups phenyl and naphthyl, and G is —COOR$_{11}$, —COR$_{13}$ or —CH$_2$OR$_{14}$, wherein $R_{13}$ is hydrogen, $C_1$–$C_6$ alkyl, the unsubstituted, mono- or di-substituted aryl groups phenyl or naphthyl, amino, mono(C1–C6)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_6$)alkyl substituted diphenylamino, mono- or di($C_1$–$C_6$)alkoxy substituted diphenylamino, morpholino, or piperidino, wherein $R_{14}$ is hydrogen, —C(O)$R_{11}$, $C_1$–$C_6$ alkyl, $C_1$–$C_3$ alkoxy($C_1$–$C_6$)alkyl, phenyl($C_1$–$C_3$)alkyl, mono($C_1$–$C_6$)alkoxy substituted phenyl($C_1$–$C_3$) alkyl, or the unsubstituted, mono- or di-substituted aryl groups phenyl or naphthyl, each of said phenyl and naphthyl group substituents being $C_1$–$C_6$ alkyl or $C_1$–$C_6$ alkoxy; and (vii) the group T represented by the formula:
—Z[(OC$_2$H$_4$)$_x$ (OC$_3$H$_6$)$_y$ (OC$_4$H$_8$)$_z$]Z'
—[(OC$_2$H$_4$)$_x$ (OC$_3$H$_6$)$_y$ (OC$_4$H$_8$)$_z$]Z'

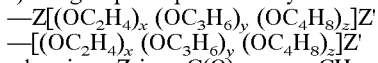

wherein —Z— is —C(O)— or —CH$_2$—, Z' is $C_1$–$C_3$ alkoxy or a polymerizable group, x, y and z are each a number between 0 and 50, and the sum of x, y and z is between 2 and 50; or (viii) $R_1$ and $R_2$ together form an oxo group, a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_2$–$C_6$ alkyl;

(b) each $R_3$ is the group T, hydrogen, $C_1$–$C_6$ alkyl, $C_1$–$C_6$ alkoxy, $C_3$–$C_7$ cycloalkyl, phenyl, benzyl, di($C_1$–$C_6$) alkylamino dicyclohexylamino, diphenylamino, piperidyl, morpholinyl, pyridyl, bromo, chloro, fluoro, or the group —C(O)W and n is the integer 0, 1, or 2, or when n is 2, and the $R_3$ groups are adjacent, the $R_3$ groups together form a fused carbocyclic or a fused heterocyclic ring selected from the group consisting of benzo, pyridino, pyrazino, pyrimidino, furano, dihydrofurano and thiopheno, said ring being fused to the n, o or p sides of the naphthopyran;

(c) $R_4$ is selected from hydrogen, $C_1$–$C_6$ alkyl, chloro or fluoro; or $R_4$, $R_5$ and $R_6$ are each selected from the group consisting of:

(i) the group, —O$R_8$', wherein $R_8$' is phenyl($C_1$–$C_3$) alkyl, $C_1$–$C_6$ alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, or $R_8$' is the group, —CH($R_9$)Q, wherein $R_9$ is hydrogen or $C_1$–$C_3$ alkyl; and (ii) a group selected from:

(1) —N($R_{15}$)$R_{16}$ wherein $R_{15}$ and $R_{16}$ are each selected from the group consisting of hydrogen, $C_1$–$C_8$ alkyl, phenyl, naphthyl, the heteroaromatic groups, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl and $C_1$–$C_{20}$ alkoxyalkyl, wherein said aryl group is phenyl or naphthyl;

(2) a nitrogen containing ring represented by the following graphic formula:

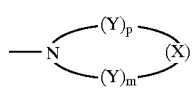

wherein Y is selected from the group consisting of —CH$_2$—, —CH($R_{17}$)—, —C($R_{17}$)($R_{17}$)—, —CH (aryl)—, —C(aryl)$_2$—, and —C($R_{17}$)(aryl)—, and X is selected from the group consisting of —Y—, —O—, —S—, —S(O)—, —S(O$_2$)—, —NH—, —N$R_{17}$— and —N-aryl, wherein $R_{17}$ is $C_1$–$C_6$ alkyl, said aryl substituent is phenyl or naphthyl, m is the integer 1, 2 or 3, and p is the integer 0, 1, 2, or 3 and when p is O, X is Y; and (3) a group represented by the following graphic formulae:

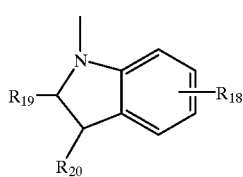 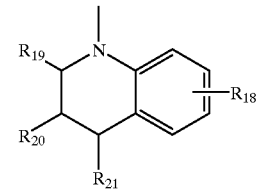

wherein $R_{19}$, $R_{20}$ and $R_{21}$ are each hydrogen, $C_1$–$C_5$ alkyl, phenyl or naphthyl, or the groups $R_{19}$ and $R_{20}$ together form a ring of 5 to 8 carbon atoms and $R_{18}$ is $C_1$–$C_6$ alkyl, $C_{1-6}$ alkoxy, fluoro or chloro; or (iii) $R_5$ and $R_6$ together form the following graphic formula:

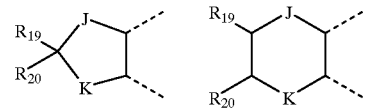

wherein J and K are each oxygen or the group —N$R_{15}$—;

(d) $R_7$ is selected from hydrogen, $C_1$–$C_6$ alkyl, chloro or fluoro;

(e) B and B' are each selected from the group consisting of:

(i) mono-T-substituted phenyl (ii) the unsubstituted, mono-, di-, and tri-substituted aryl groups, phenyl and naphthyl;

(iii) 9-julolidinyl and the unsubstituted, mono- and di-substituted heteroaromatic groups, pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of said aryl and heteroaromatic substituents in (e) (ii) and (iii) being selected from the group consisting of hydroxy, aryl, mono($C_1$–$C_6$) alkoxyaryl, di($C_1$–$C_6$)alkoxyaryl, mono($C_1$–$C_6$) alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$) alkyl, aryl($C_1$–$C_6$)alkoxy, aryloxy, aryloxy($C_1$–$C_6$) alkyl, aryloxy($C_1$–$C_6$)alkoxy, mono- and di-($C_1$–$C_6$) alkylaryl($C_1$–$C_6$)alkyl, mono- and di-($C_1$–$C_6$) alkoxyaryl($C_1$–$C_6$)alkyl, mono- and di-($C_1$–$C_6$) alkylaryl($C_1$–$C_6$)alkoxy, mono- and di-($C_1$–$C_6$) alkoxyaryl($C_1$–$C_6$)alkoxy, amino, mono($C_1$–$C_6$) alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, said aryl being phenyl or naphthyl;

(iv) the unsubstituted or mono-substituted groups pyrazolyl, imidazolyl, pyrazolinyl, imidazolinyl, pyrrolinyl, phenothiazinyl, phenoxazinyl, phenazinyl or acridinyl, each of said substituents being selected from the group consisting of $C_1$–$C_6$ alkyl, $C_1$–$C_6$ alkoxy, phenyl, fluoro, chloro and bromo;

(v) monosubstituted phenyl, having a substituent at the para position that is a linking group, —$(CH_2)_t$— or —O—$(CH_2)_t$—, wherein t is the integer 1, 2, 3, 4, 5 or 6, connected to an aryl group, which is a member of another photochromic naphthopyran;

(vi) the groups represented by the following graphic formulae:

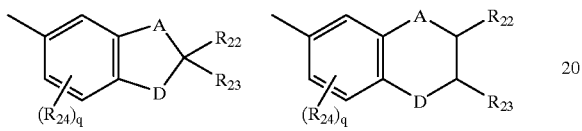

wherein A is methylene or oxygen and D is oxygen or substituted nitrogen, provided that when D is substituted nitrogen, A is methylene, said nitrogen substituents being selected from the group consisting of hydrogen, $C_1$–$C_6$ alkyl, and $C_2$–$C_6$ acyl; each $R_{24}$ is $C_1$–$C_6$ alkyl, $C_1$–$C_6$ alkoxy, hydroxy, chloro or fluoro; $R_{22}$ and $R_{23}$ are each hydrogen or $C_1$–$C_6$ alkyl; and q is the integer 0, 1, or 2;

(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$) cycloalkyl, chloro ($C_3$–$C_6$)cycloalkyl, fluoro($C_3$–$C_6$)cyclo-alkyl and $C_4$–$C_{12}$ bicycloalkyl; and (viii) the group represented by the following graphic formula:

wherein L is hydrogen or $C_1$–$C_4$ alkyl and M is selected from the unsubstituted, mono-, and di-substituted members of the group consisting of naphthyl, phenyl, furanyl, and thienyl, each of said group substituents being $C_1$–$C_4$ alkyl, $C_1$–$C_4$ alkoxy, fluoro, or chloro; or (f) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

3. The naphthopyran of claim 2 wherein, (a) $R_1$ and $R_2$ are each selected from the group consisting of hydrogen, hydroxy, $C_1$–$C_4$ alkyl, $C_3$–$C_6$ cycloalkyl, chloro, fluoro and the group, —$OR_8$, wherein $R_8$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl, $C_1$–$C_3$ fluoroalkyl, the group, —CH($R_9$)Q, wherein $R_9$ is hydrogen or $C_1$–$C_2$ alkyl and Q is —CN or —$COOR_{10}$, and $R_{10}$ is hydrogen or $C_1$–$C_2$ alkyl, or $R_8$ is the group, —C(O)V, wherein V is hydrogen, $C_1$–$C_3$ alkyl, $C_1$–$C_3$ alkoxy, phenyl, naphthyl, the mono-substituted aryl groups, phenyl or naphthyl, phenoxy, mono- or di-($C_1$–$C_3$)alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, and said aryl substituents being $C_1$–$C_3$ alkyl or $C_1$–$C_3$ alkoxy, or $R_1$ and $R_2$ are each the group T, x and y are each a number between 0 and 50, z is 0 and the sum of x and y is between 2 and 50;

(b) $R_3$ is $C_1$–$C_6$ alkyl, $C_1$–$C_6$ alkoxy, chloro or fluoro;

(c) $R_4$ is selected from hydrogen, $C_1$–$C_3$ alkyl, chloro or fluoro; or $R_4$, $R_5$ and $R_6$ are each selected from the group consisting of (i) the group, —$OR_8'$, wherein $R_8'$ is —CH($R_9$)Q and Q is —CN; and (ii) a group selected from:

(1) —N($R_{15}$)$R_{16}$, wherein $R_{15}$ and $R_{16}$ are $C_1$–$C_4$ alkyl;

(2) a nitrogen containing ring represented by the graphic formula:

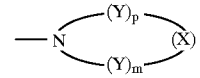

wherein Y is —$CH_2$— or —CH($R_{17}$)—, X is —O—, —NH— or —$NR_{17}$— and $R_{17}$ is $C_1$–$C_3$ alkyl;

(3) a group represented by the following graphic formulae:

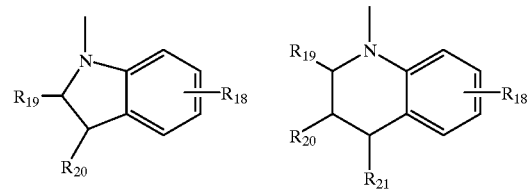

wherein $R_{19}$, $R_{20}$ and $R_{21}$ are each hydrogen or $C_1$–$C_3$ alkyl and $R_{18}$ is $C_1$–$C_3$ alkyl; or (iii) $R_5$ and $R_6$ together form the following graphic formulae:

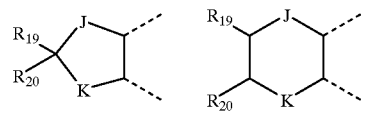

wherein J and K are oxygen;

(d) $R_7$ is selected from hydrogen, $C_1$–$C_3$ alkyl, chloro or fluoro;

(e) B and B' are each selected from the group consisting of:

(i) phenyl, mono-substituted phenyl, and di-substituted phenyl;

(ii) the unsubstituted, mono-, and di-substituted aromatic heterocyclic groups furanyl, benzofuran-2-yl, thienyl, benzothien-2-yl and dibenzofuranyl, said phenyl and aromatic heterocyclic substituents in (e)(i) and (ii) being selected from the group consisting of hydroxy, amino, mono($C_1$–$C_3$)alkyl-amino, di($C_1$–$C_3$)alkylamino, piperidino, morpholino, pyrrolidyl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy ($C_1$–$C_3$)alkyl, fluoro and chloro;

(iii) the groups represented by the following graphic formulae:

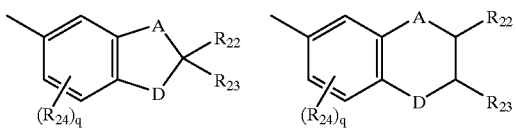

wherein A is methylene and D is oxygen, $R_{24}$ is $C_1$–$C_3$ alkyl or $C_1$–$C_3$ alkoxy, $R_{22}$ and $R_{23}$ are each hydrogen or $C_1$–$C_4$ alkyl; and q is the integer 0 or 1;

(iv) $C_1$–$C_4$ alkyl; and (v) the group represented by the following graphic formula:

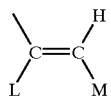

herein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (f) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-xylidene substituent being selected from the group consisting of $C_1$–$C_3$ alkyl, $C_1$–$C_3$ alkoxy, fluoro and chloro.

4. The naphthopyran compound of claim 3 wherein, (a) $R_1$ and $R_2$ are each hydrogen, $C_1$–$C_3$ alkyl, the group, —$OR_8$, wherein $R_8$ is $C_1$–$C_3$ alkyl or, $R_1$ and $R_2$ are each the group T and x is a number between 2 and 50, y and z are each 0;

(b) $R_3$ is $C_1$–$C_3$ alkoxy;

(c) $R_4$ is hydrogen; or $R_4$, $R_5$ and $R_6$ are each $C_1$–$C_3$ alkoxy;

(d) $R_7$ is hydrogen; and (e) B and B' are each selected from the group consisting of phenyl, mono-, and di-substituted phenyl, unsubstituted, mono-, and di-substituted aromatic heterocyclic groups furanyl, benzofuran-2-yl, thienyl, benzothien-2-yl, and dibenzofuranyl each of said phenyl and aromatic heterocyclic substituents being selected from the group consisting of hydroxy, $C_1$–$C_3$ alkyl, $C_1$–$C_3$ alkoxy, fluoro and chloro; and the group represented by the following graphic formula:

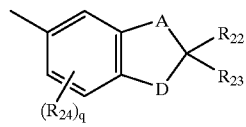

wherein A is methylene and D is oxygen, $R_{24}$ is $C_1$–$C_3$ alkyl or $C_1$–$C_3$ alkoxy, $R_{22}$ and $R_{23}$ are each hydrogen or $C_1$–$C_3$ alkyl, and q is the integer 0 or 1; or B and B' taken together form fluoren-9-ylidene, adamantylidene, bornylidene, norbornylidene, or bicyclo(3.3.1)nonan-9-ylidene.

5. A naphthopyran compound selected from the group consisting of:

(a) 3,3-di(4-methoxyphenyl)-6,7,10,11-tetramethoxy-13,13-dimethyl-3H,13H-indeno[2,1-f]naphtho[1,2-b]pyran;

(b) 3-phenyl-3-(4-morpholinophenyl)-6,7,10,11-tetramethoxy-13,13-dimethyl-3H,13H-indeno[2,1-f]naphtho[1,2-b]pyran;

(c) 3,3-di(4-methoxyphenyl)-6,7,10,11-tetramethoxy-13-hydroxy-13-ethyl-3H,13H-indeno[2,1-f]naphtho[1,2-b]pyran;

(d) 3,3-di(4-methoxyphenyl)-6,7-dimethoxy-13,13-dimethyl-3H,13H-indeno[2,1-f]naphtho[1,2-b]pyran;

(e) 3,3-di(4-methoxyphenyl)-6,7-dimethoxy-13-hydroxy-13-ethyl-3H,13H-indeno[2,1-f]naphtho[1,2-b]pyran;

(f) 3,3-di(4-methoxyphenyl)-6,7,10,11-tetramethoxy-13,13-diethyl-3H,13H-indeno[2,1-f]naphtho[1,2-b]pyran;

(g) 3,3-di(4-methoxyphenyl)-6,7-dimethoxy-13-phenyl-3H,13H-indeno[2,1-f]naphtho1,2-b]pyran;

(h) 3-(4-methoxyphenyl)-3-(4-morpholinophenyl)-6,7-dimethoxy-13-phenyl-3H,13H-indeno[2,1-f]naphtho[1,2-b]pyran;

(i) 3-(4-methoxyphenyl)-3-(4-morpholinophenyl)-6,7-dimethoxy-13,13-dimethyl-3H,13H-indeno[2,1-f]naphtho[1,2-b]pyran;

(j) 3-(4-methoxyphenyl)-3-(4-dimethylaminophenyl)-6,7-dimethoxy-13,13-dimethyl-3H,13H-indeno[2,1-f]naphtho[1,2-b]pyran;

(k) 3,3-di(4-methoxyphenyl)-6,7,8-trimethoxy-13-phenyl-3H,13H-indeno[2,1-f]naphtho[1,2-b]pyran;

(l) 3-(4-methoxyphenyl)-3-(4-morpholinophenyl)-6,7,10,11-tetramethoxy-13-hydroxy-13-ethyl-3H,13H-indeno[2,1-f]naphtho[1,2-b]pyran;

(m) 3-(4-methoxyphenyl)-3-(4-morpholinophenyl)-6,7,10,11-tetramethoxy-13-hydroxy-13-butyl-3H,13H-indeno[2,1-f]naphtho[1,2-b]pyran;

(n) 3-(4-morpholinophenyl)-3-phenyl-6,7-dimethoxy-13-hydroxy-13-ethyl-3H,13H-indeno[2,1,-f]naphtho[1,2-b]pyran;

(o) 3,3-di(4-methoxyphenyl)-6,7-dimethoxy-13-hydroxy-13-butyl-3H,13H-indeno[2,1,-f]naphtho[1,2-b]pyran;

(p) 3-(4-morpholinophenyl)-3-phenyl-6,7-dimethoxy-13-hydroxy-13-butyl-3H,13H-indeno[2,1,-f]naphtho[1,2-b]pyran;

(q) 3-(4-methoxyphenyl)-3-(4-morpholinophenyl)-6,7-dimethoxy-13-hydroxy-13-ethyl-3H,13H-indeno[2,1-f]naphtho[1,2-b]pyran;

(r) 3-(4-methoxyphenyl)-3-(4-morpholinophenyl)-6,7-dimethoxy-13-ethyl-13-methoxy-3H,13H-indeno[2,1-f]naphtho[1,2-b]pyran;

(s) 3-(4-methoxyphenyl)-3-(4-morpholinophenyl)-5 6,7-dimethoxy-13-hydroxy-13-methyl-3H,13H-indeno[2,1-f]naphtho[1,2-b]pyran; and (t) 3-(4-methoxyphenyl)-3-(4-morpholinophenyl)-6,7-dimethoxy-13-methoxy-13-methyl-3H,13H-indeno[2,1-f]naphtho[1,2-b]pyran.

6. A photochromic article comprising a polymeric organic host material and a photochromic amount of the naphthopyran compound of claim 1.

7. The photochromic article of claim 6 wherein the polymeric organic host material is selected from the group consisting of poly($C_1$–$C_{12}$ alkyl methacrylates), poly (oxyalkylene) dimethacrylates, poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

8. The photochromic article of claim 7 wherein the polymeric organic host material is a solid transparent polymer selected from the group consisting of poly(methyl methacrylate), poly(ethylene glycol) bismethacrylate, poly (ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

9. The photochromic article of claim 8 wherein the photochromic compound is present in an amount of from about 0.05 to 2.0 milligram per square centimeter of organic host material surface to which the photochromic substance (s) is incorporated or applied.

10. The photochromic article of claim 9 wherein the article is a lens.

11. A photochromic article comprising a polymeric organic host material selected from the group consisting of poly(methyl methacrylate), polyethylene glycol) bismethacrylate, poly(ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers and a photochromic amount of the naphthopyran compound of claim 2.

12. A photochromic article comprising a polymeric organic host material selected from the group consisting of poly(methyl methacrylate), poly(ethylene glycol) bismethacrylate, poly(ethoxylated bisphenol A) dimethacrylate, thermoplastic polycarbonate, polylvinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of the naphthopyran compound of claim 3.

13. A photochromic article comprising a polymerizate of an optical organic resin monomer and a photochromic amount of the naphthopyran compound of claim 1.

14. The photochromic article of claim 13 wherein the refractive index of the polymerizate is from about 1.48 to about 1.75.

15. The photochromic article of claim 13 wherein the polymerizate is an optical element.

16. The photochromic article of claim 15 wherein said optical element is an ophthalmic lens or a contact lens.

17. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

18. The photochromic article of claim 17 wherein the polymeric organic host material is a solid transparent homopolymer or copolymer selected from the group consisting of poly(methyl methacrylate), poly(ethylene glycol bis methacrylate), poly(ethoxylated bisphenol A) dimethacrylate, thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers.

19. The photochromic article of claim 17 wherein the organic photochromic compound (b) is selected from the group consisting of naphthopyrans, benzopyrans, phenanthropyrans, indenonaphthopyrans, oxazine, metal-dithiozonates, fulgides, fulgimides, spiro(indoline)pyrans, and mixtures of such photochromic compounds.

20. The photochromic article of claim 19 wherein the photochromic compound is present in an amount of from about 0.05 to 2.0 milligram per square centimeter of organic host material surface to which the photochromic substance (s) is incorporated or applied.

21. The photochromic article of claim 20 wherein the article is an ophthalmic lens or a contact lens.

22. A photochromic article comprising, in combination, a polymeric organic host material selected from the group consisting of poly(methyl methacrylate), poly(ethylene glycol) bismethacrylate, poly(ethoxylated bisphenol A) dimethacrylate, thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 2, and (b) at least one other organic photochromic compound having at least one activated absorption maxima within the range of between about 400 and 700 nanometers.

23. A photochromic article comprising, in combination, a polymeric organic host material selected from the group consisting of poly(methyl methacrylate), poly ethylene glycol) bismethacrylate, poly ethoxylated bisphenol A) dimethacrylate, thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

* * * * *

UNITED STATES PATENT AND TRADEMARK OFFICE
CERTIFICATE OF CORRECTION

PATENT NO. : 6,296,785 B1
DATED : October 2, 2001
INVENTOR(S) : Nelson et al.

It is certified that error appears in the above-identified patent and that said Letters Patent is hereby corrected as shown below:

Column 53,
Line 25, "—(O)—" should be -- —S(O)— --.

Column 55,
Line 11, please insert the word -- or -- at the end of the line.

Column 60,
Line 65, "3—(4—methoxyphenyl)—3—(4—morpholinophenyl)—5" should be
-- 3—(4—methoxyphenyl)—3—(4—morpholinophenyl)— --.

Column 61,
Line 49, "poly(methyl methacrylate), polyethylene glycol" should be
-- poly(methyl methacrylate), poly(ethylene glycol) --.

Signed and Sealed this

Seventeenth Day of September, 2002

*Attest:*

*Attesting Officer*

JAMES E. ROGAN
*Director of the United States Patent and Trademark Office*